(12) United States Patent
Spodsberg

(10) Patent No.: US 8,759,041 B1
(45) Date of Patent: Jun. 24, 2014

(54) POLYPEPTIDES HAVING XYLANASE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignee: Novozymes Inc., Davis, CA (US)

( * ) Notice: Subject to any disclaimer, the term of this patent is extended or adjusted under 35 U.S.C. 154(b) by 0 days.

(21) Appl. No.: 13/765,286

(22) Filed: Feb. 12, 2013

(51) Int. Cl.
*C12N 9/42* (2006.01)
*C12N 9/24* (2006.01)

(52) U.S. Cl.
CPC ............................... *C12N 9/248* (2013.01)
USPC ............ 435/99; 435/200; 435/196; 435/189; 435/212; 435/219; 435/209; 435/100; 435/101; 435/105; 435/106; 435/132; 435/136; 435/148; 435/155; 435/161; 435/160; 435/166; 435/168

(58) Field of Classification Search
None
See application file for complete search history.

(56) References Cited

U.S. PATENT DOCUMENTS

| | | | | |
|---|---|---|---|---|
| 4,966,850 A * | 10/1990 | Yu et al. | ......................... | 435/200 |
| 5,306,633 A * | 4/1994 | Gottschalk et al. | ............ | 435/200 |
| 5,358,864 A * | 10/1994 | van den Broeck et al. | ... | 435/209 |
| 5,610,048 A * | 3/1997 | Schulein et al. | .............. | 435/209 |
| 5,658,765 A * | 8/1997 | Noguchi et al. | ................ | 435/99 |
| 5,688,668 A * | 11/1997 | Sj.o slashed.holm et al. | .. | 435/74 |
| 5,696,068 A * | 12/1997 | Outtrup et al. | ................ | 510/392 |
| 5,824,533 A * | 10/1998 | Li et al. | ........................... | 435/209 |
| 5,871,730 A * | 2/1999 | Brzezinski et al. | ......... | 424/94.61 |
| 5,902,581 A * | 5/1999 | Clarkson et al. | ........... | 424/94.61 |
| 5,916,795 A * | 6/1999 | Fukunaga et al. | ............. | 435/200 |
| 6,017,749 A * | 1/2000 | Outtrup et al. | .............. | 435/252.5 |
| 6,121,034 A * | 9/2000 | Laroche et al. | ................ | 435/209 |
| 6,140,097 A * | 10/2000 | Okada et al. | ................... | 435/209 |
| 6,346,407 B1 * | 2/2002 | De Buyl et al. | ................ | 435/200 |
| 6,534,101 B1 * | 3/2003 | Sabatier et al. | .................. | 426/53 |
| 6,586,209 B1 * | 7/2003 | van Gorcom et al. | ........ | 435/69.2 |
| 6,682,923 B1 * | 1/2004 | Bentzien et al. | .............. | 435/209 |
| 6,815,192 B2 * | 11/2004 | Schnorr et al. | ................. | 435/210 |
| 7,635,471 B2 * | 12/2009 | Cheng et al. | ............... | 424/94.61 |
| 2006/0003433 A1 * | 1/2006 | Steer et al. | ..................... | 435/209 |
| 2008/0187627 A1 * | 8/2008 | Bauer et al. | ....................... | 426/53 |
| 2009/0203079 A1 * | 8/2009 | Sticklen et al. | ................. | 435/72 |
| 2012/0135474 A1 * | 5/2012 | Cann et al. | ...................... | 435/99 |
| 2012/0240293 A1 * | 9/2012 | Tang et al. | ..................... | 800/298 |
| 2013/0109062 A1 * | 5/2013 | Kohl et al. | ....................... | 435/99 |
| 2013/0130325 A1 * | 5/2013 | Morant | ........................... | 435/99 |
| 2013/0130326 A1 * | 5/2013 | Morant | ........................... | 435/99 |
| 2013/0130327 A1 * | 5/2013 | Morant | ........................... | 435/99 |
| 2013/0180013 A1 * | 7/2013 | Spodsberg | .................... | 800/298 |
| 2013/0212746 A1 * | 8/2013 | Spodsberg et al. | ........... | 800/298 |
| 2013/0273611 A1 * | 10/2013 | Steffens et al. | ................. | 435/99 |

FOREIGN PATENT DOCUMENTS

| | | | |
|---|---|---|---|
| WO | WO 9118978 A1 * | 12/1991 | |
| WO | WO 9203540 A1 * | 3/1992 | |
| WO | WO 2009108941 A2 * | 9/2009 | |

OTHER PUBLICATIONS

GenBank Accession No. AEJ35165; GI: 339219002; published Jul. 6, 2011.*

* cited by examiner

*Primary Examiner* — Rebecca Prouty
*Assistant Examiner* — Richard Ekstrom
(74) *Attorney, Agent, or Firm* — Elias Lambiris

(57) ABSTRACT

The present invention relates to isolated polypeptides having xylanase activity and polynucleotides encoding the polypeptides. The invention also relates to nucleic acid constructs, vectors, and host cells comprising the polynucleotides as well as methods of producing and using the polypeptides.

19 Claims, No Drawings

SEQUENCE LISTING

```
<160> NUMBER OF SEQ ID NOS: 10

<210> SEQ ID NO 1
<211> LENGTH: 1396
<212> TYPE: DNA
<213> ORGANISM: Hohenbuehelia mastrucata
<220> FEATURE:
<221> NAME/KEY: CDS
<222> LOCATION: (1)..(204)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (205)..(254)
<220> FEATURE:
<221> NAME/KEY: CDS
<222> LOCATION: (255)..(345)
<220> FEATURE:
<221> NAME/KEY: Intron
<222> LOCATION: (346)..(399)
<220> FEATURE:
<221> NAME/KEY: CDS
<222> LOCATION: (400)..(526)
<220> FEATURE:
<221> NAME/KEY: Intron
<222> LOCATION: (527)..(580)
<220> FEATURE:
<221> NAME/KEY: CDS
<222> LOCATION: (581)..(582)
<220> FEATURE:
<221> NAME/KEY: Intron
<222> LOCATION: (583)..(644)
<220> FEATURE:
<221> NAME/KEY: CDS
<222> LOCATION: (645)..(665)
<220> FEATURE:
<221> NAME/KEY: Intron
<222> LOCATION: (666)..(716)
<220> FEATURE:
<221> NAME/KEY: CDS
<222> LOCATION: (717)..(1168)
<220> FEATURE:
<221> NAME/KEY: Intron
<222> LOCATION: (1169)..(1231)
<220> FEATURE:
<221> NAME/KEY: CDS
<222> LOCATION: (1232)..(1288)
<220> FEATURE:
<221> NAME/KEY: Intron
<222> LOCATION: (1289)..(1345)
<220> FEATURE:
<221> NAME/KEY: CDS
<222> LOCATION: (1346)..(1393)

<400> SEQUENCE: 1 atg aaa tcc gcc ctc ttg gtc ctc acg gtg aca gtg cct ttc gct gca      48
Met Lys Ser Ala Leu Leu Val Leu Thr Val Thr Val Pro Phe Ala Ala
                -15                 -10                 -5 gca cag gca ggg ttg aat agg gtg gcg aaa gca gct ggg aag cta tac      96
Ala Gln Ala Gly Leu Asn Arg Val Ala Lys Ala Ala Gly Lys Leu Tyr
            -1   1               5                  10 ttt ggg aca gca aca aac ctg gaa caa ttc acg gat gcg cca tac ttt     144
Phe Gly Thr Ala Thr Asn Leu Glu Gln Phe Thr Asp Ala Pro Tyr Phe
     15                  20                  25
```

```
gcc gtg ctg aac aat gtc acc gag ttc gga cag atc act gcc gca aat        192
Ala Val Leu Asn Asn Val Thr Glu Phe Gly Gln Ile Thr Ala Ala Asn
 30              35                  40                  45 agc atg aaa tgg gtacgttcac gcgatttcgt gcgtattata tatgctgact            244
Ser Met Lys Trp tgcatcaaag gat gcg acc gaa ccc tct agg ggc gtc ttc acc ttc gct         293
           Asp Ala Thr Glu Pro Ser Arg Gly Val Phe Thr Phe Ala
            50                  55                  60 caa gga gat caa atc gcg gct ctc gcg cag cag aac ggc cag ctt ctt        341
Gln Gly Asp Gln Ile Ala Ala Leu Ala Gln Gln Asn Gly Gln Leu Leu
             65                  70                  75 aga g gtcagtgccg tatcattgaa ccaaaccgag cggggtgatt atcttccgcc gcag      399
Arg gt  cac aat tgt gtc tgg cac caa cag ctc cct gcc tgg gtc aca gac        446
Gly His Asn Cys Val Trp His Gln Gln Leu Pro Ala Trp Val Thr Asp
 80              85                  90                  95 gga aac ttt gat gcc cca acc tta acg agt att gtt gag act cat tgc        494
Gly Asn Phe Asp Ala Pro Thr Leu Thr Ser Ile Val Glu Thr His Cys
                100                 105                 110 tca aca atc gtt gat cat tac aaa ggc caa at  gtcagttagt ttccatgatc     546
Ser Thr Ile Val Asp His Tyr Lys Gly Gln Ile
                115                 120 gccgcgacga atactaaaga gtacttgttt tcag a t gtatgactca cttgagagcc        602
atgtgcacag aaacatgctg atatgatttt ccttgacttt ag ac  agc tgg gat        655
                                                  Ser Trp Asp
                                                      125 gtc atc aac g gtgagccaga atgtcgttgc tgatcaatta ctttgcttat              705
Val Ile Asn acaatactta g ag  tgc ctg aat gac gac ggc acg ttc cgc gag gat gtc      754
              Glu Cys Leu Asn Asp Asp Gly Thr Phe Arg Glu Asp Val
               130                 135                 140 ttc ttc gat acc ctg aac acc tcg tac atc gcc act gcc ctt cgc gca        802
Phe Phe Asp Thr Leu Asn Thr Ser Tyr Ile Ala Thr Ala Leu Arg Ala
            145                 150                 155 gca cgc gcc gcc gac cca aac gca aag ctc tac ata aac gac ttc aat        850
Ala Arg Ala Ala Asp Pro Asn Ala Lys Leu Tyr Ile Asn Asp Phe Asn
        160                 165                 170 atc gag ggc acc ggt cca aaa tcc acc gct atg gtc aac ctg gtc aag        898
Ile Glu Gly Thr Gly Pro Lys Ser Thr Ala Met Val Asn Leu Val Lys
175             180                 185                 190 tcc ctt caa gct caa aac gtg ccg atc gac ggc att ggc atc caa acc        946
Ser Leu Gln Ala Gln Asn Val Pro Ile Asp Gly Ile Gly Ile Gln Thr
                195                 200                 205 cac ctc atc gtc ggc gag gtc cca agc acg ctc ctc gaa aac atg cag        994
His Leu Ile Val Gly Glu Val Pro Ser Thr Leu Leu Glu Asn Met Gln
            210                 215                 220 caa ttc acg gcg ttg ggc gtg gag atc gct att act gag ttg gat atc        1042
Gln Phe Thr Ala Leu Gly Val Glu Ile Ala Ile Thr Glu Leu Asp Ile
        225                 230                 235 cgc atg acc ctt ccc gat acg cca gag ctg cgt gct caa caa cag cag        1090
Arg Met Thr Leu Pro Asp Thr Pro Glu Leu Arg Ala Gln Gln Gln Gln
240                 245                 250 gat tac cag act gtc atc gag gct tgt aac aca gtg ccc gaa tgt gtg        1138
Asp Tyr Gln Thr Val Ile Glu Ala Cys Asn Thr Val Pro Glu Cys Val
255                 260                 265                 270 ggt gtg act gta tgg gat ttc acc gac aag gtacgaggtg ttcgttcctc          1188
Gly Val Thr Val Trp Asp Phe Thr Asp Lys
                275                 280 gaggaagctg caggagctaa tctgagccgc tgtgtgccca cag tat tcg tgg gtc        1243
```

```
                                        Tyr Ser Trp Val cca ggt act ttc aca ggc caa gga gat gct tgt cca tgg gac gag    1288
Pro Gly Thr Phe Thr Gly Gln Gly Asp Ala Cys Pro Trp Asp Glu
285                 290                 295 gtgggtgatt gcacgccaca tcattttgct gcgaaactga tgcgaggcgg ctctcag  1345 aat atc gtc agg aag tca gcg tac gat ggt att gtg gca ggg ttc gcg    1393
Asn Ile Val Arg Lys Ser Ala Tyr Asp Gly Ile Val Ala Gly Phe Ala
300             305                 310                 315 tga                                                             1396

<210> SEQ ID NO 2
<211> LENGTH: 334
<212> TYPE: PRT
<213> ORGANISM: Hohenbuehelia mastrucata

<400> SEQUENCE: 2

Met Lys Ser Ala Leu Leu Val Leu Thr Val Thr Val Pro Phe Ala Ala
                -15                 -10                 -5

Ala Gln Ala Gly Leu Asn Arg Val Ala Lys Ala Ala Gly Lys Leu Tyr
        -1  1                 5                   10

Phe Gly Thr Ala Thr Asn Leu Glu Gln Phe Thr Asp Ala Pro Tyr Phe
        15                  20                  25

Ala Val Leu Asn Asn Val Thr Glu Phe Gly Gln Ile Thr Ala Ala Asn
30                  35                  40                  45

Ser Met Lys Trp Asp Ala Thr Glu Pro Ser Arg Gly Val Phe Thr Phe
                50                  55                  60

Ala Gln Gly Asp Gln Ile Ala Ala Leu Ala Gln Gln Asn Gly Gln Leu
            65                  70                  75

Leu Arg Gly His Asn Cys Val Trp His Gln Gln Leu Pro Ala Trp Val
        80                  85                  90

Thr Asp Gly Asn Phe Asp Ala Pro Thr Leu Thr Ser Ile Val Glu Thr
    95                  100                 105

His Cys Ser Thr Ile Val Asp His Tyr Lys Gly Gln Ile Tyr Ser Trp
110                 115                 120                 125

Asp Val Ile Asn Glu Cys Leu Asn Asp Gly Thr Phe Arg Glu Asp
                130                 135                 140

Val Phe Phe Asp Thr Leu Asn Ser Tyr Ile Ala Thr Ala Leu Arg
            145                 150                 155

Ala Ala Arg Ala Ala Asp Pro Asn Ala Lys Leu Tyr Ile Asn Asp Phe
        160                 165                 170

Asn Ile Glu Gly Thr Gly Pro Lys Ser Thr Ala Met Val Asn Leu Val
    175                 180                 185

Lys Ser Leu Gln Ala Gln Asn Val Pro Ile Asp Gly Ile Gly Ile Gln
190                 195                 200                 205

Thr His Leu Ile Val Gly Glu Val Pro Ser Thr Leu Leu Glu Asn Met
                210                 215                 220

Gln Gln Phe Thr Ala Leu Gly Val Glu Ile Ala Ile Thr Glu Leu Asp
            225                 230                 235

Ile Arg Met Thr Leu Pro Asp Thr Pro Glu Leu Arg Ala Gln Gln Gln
        240                 245                 250

Gln Asp Tyr Gln Thr Val Ile Glu Ala Cys Asn Thr Val Pro Glu Cys
    255                 260                 265

Val Gly Val Thr Val Trp Asp Phe Thr Asp Lys Tyr Ser Trp Val Pro
270                 275                 280                 285

Gly Thr Phe Thr Gly Gln Gly Asp Ala Cys Pro Trp Asp Glu Asn Ile
```

```
                        290                 295                 300
Val Arg Lys Ser Ala Tyr Asp Gly Ile Val Ala Gly Phe Ala
            305                 310                 315

<210> SEQ ID NO 3
<211> LENGTH: 1402
<212> TYPE: DNA
<213> ORGANISM: Hohenbuehelia mastrucata
<220> FEATURE:
<221> NAME/KEY: CDS
<222> LOCATION: (1)..(204)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (205)..(266)
<220> FEATURE:
<221> NAME/KEY: CDS
<222> LOCATION: (267)..(357)
<220> FEATURE:
<221> NAME/KEY: Intron
<222> LOCATION: (358)..(410)
<220> FEATURE:
<221> NAME/KEY: CDS
<222> LOCATION: (411)..(537)
<220> FEATURE:
<221> NAME/KEY: Intron
<222> LOCATION: (538)..(594)
<220> FEATURE:
<221> NAME/KEY: CDS
<222> LOCATION: (595)..(602)
<220> FEATURE:
<221> NAME/KEY: Intron
<222> LOCATION: (603)..(655)
<220> FEATURE:
<221> NAME/KEY: CDS
<222> LOCATION: (656)..(676)
<220> FEATURE:
<221> NAME/KEY: Intron
<222> LOCATION: (677)..(726)
<220> FEATURE:
<221> NAME/KEY: CDS
<222> LOCATION: (727)..(1182)
<220> FEATURE:
<221> NAME/KEY: Intron
<222> LOCATION: (1183)..(1247)
<220> FEATURE:
<221> NAME/KEY: CDS
<222> LOCATION: (1248)..(1297)
<220> FEATURE:
<221> NAME/KEY: Intron
<222> LOCATION: (1298)..(1351)
<220> FEATURE:
<221> NAME/KEY: CDS
<222> LOCATION: (1352)..(1399)

<400> SEQUENCE: 3 atg aag ctc gtg cct gtc ctc att gca att tct gca acc ttg gct gct      48
Met Lys Leu Val Pro Val Leu Ile Ala Ile Ser Ala Thr Leu Ala Ala
                -15                 -10                 -5 gct cag gcg ggg tta aat aaa gtg gcc aag gcc gcc ggg aag aaa tat      96
Ala Gln Ala Gly Leu Asn Lys Val Ala Lys Ala Ala Gly Lys Lys Tyr
        -1  1               5                   10 ttc ggg acc gcg act aat aat aac gag ttc aca gac gct tcc tat ttc     144
Phe Gly Thr Ala Thr Asn Asn Asn Glu Phe Thr Asp Ala Ser Tyr Phe
     15                  20                  25 cct gta ctg aat aac gtc act gat ttt ggg cag att acc gca gca att     192
Pro Val Leu Asn Asn Val Thr Asp Phe Gly Gln Ile Thr Ala Ala Ile
30                  35                  40                  45
```

|   |   |
|---|---|
| agc atg aaa tgg gtatatccat ccattatcct gtttctggga gacaaccttg<br>Ser Met Lys Trp | 244 |
| ctcacttccg agtcgttctt ag gac gca acg gag cca tct cgt ggt aca ttt<br>Asp Ala Thr Glu Pro Ser Arg Gly Thr Phe<br>50        55 | 296 |
| acg ttt gcg cag ggg aat gaa att gcc gca ctt gcc ata aag aac ggc<br>Thr Phe Ala Gln Gly Asn Glu Ile Ala Ala Leu Ala Ile Lys Asn Gly<br>60            65                  70                  75 | 344 |
| cag tta ctt cga g gttgtgtcgt atctgctcaa tcacgtttta gttgattcat<br>Gln Leu Leu Arg | 397 |
| ttcctgcccg cag gc cat aac tgt gta tgg cat cag caa ctc cct tcg<br>        Gly His Asn Cys Val Trp His Gln Gln Leu Pro Ser<br>            80                  85                  90 | 445 |
| tgg gtc acc agt ggg aac ttc gat gta cca aca cta cca agc atc gtc<br>Trp Val Thr Ser Gly Asn Phe Asp Val Pro Thr Leu Pro Ser Ile Val<br>            95                 100                 105 | 493 |
| tcg agc cac tgt cta ccc ttg tgg gac gct ata gag ggc cta gt<br>Ser Ser His Cys Leu Pro Leu Trp Asp Ala Ile Glu Gly Leu Val<br>110                 115                 120 | 537 |
| gtgagtgctc cggctatgcc agcagtcacg attgtactga tctccattga tttacag c | 595 |
| tgt atg t gtagcattgc attgacaatg gatatggttt cttattcaca ctttcgtcgc<br>Cys Met | 652 |
| tag at agc tgg gat gtc atc aat g gtgcgcgggc tgttgattac<br>    Tyr Ser Trp Asp Val Ile Asn<br>    125                 130 | 696 |
| agtcgatgcc tatcttcaac tgcgctacag aa tgc ttg aga gat gac gga acc<br>                                    Glu Cys Leu Arg Asp Asp Gly Thr<br>                                                    135 | 749 |
| ttc cgc tca gat gtt ttc tcc agg acc ctc ggg acc tca tac atc gcc<br>Phe Arg Ser Asp Val Phe Ser Arg Thr Leu Gly Thr Ser Tyr Ile Ala<br>140                 145                 150                 155 | 797 |
| act gcc ttg cgt gca gcg cgt gcc gcc gac cca acc gcc aag ctt tac<br>Thr Ala Leu Arg Ala Ala Arg Ala Ala Asp Pro Thr Ala Lys Leu Tyr<br>            160                 165                 170 | 845 |
| atc agt gac ttc aac atc gaa ggc acc gga gcc aag tcc acc gcc atg<br>Ile Ser Asp Phe Asn Ile Glu Gly Thr Gly Ala Lys Ser Thr Ala Met<br>            175                 180                 185 | 893 |
| gtg aat ctc gtt aaa ttc ctc caa tcg cag ggc gtg cct atc gac ggc<br>Val Asn Leu Val Lys Phe Leu Gln Ser Gln Gly Val Pro Ile Asp Gly<br>            190                 195                 200 | 941 |
| atc ggg atc cag gcg cat ctc att gtc ggt aaa gtc cgg agc aca cta<br>Ile Gly Ile Gln Ala His Leu Ile Val Gly Lys Val Arg Ser Thr Leu<br>            205                 210                 215 | 989 |
| gtc gcg aat atg cgc cag ttc acg gca ttg ggt gtg gaa att gcc ttt<br>Val Ala Asn Met Arg Gln Phe Thr Ala Leu Gly Val Glu Ile Ala Phe<br>220                 225                 230                 235 | 1037 |
| acc gag ctg gac att cga atg gcg ctc tct gcg acg ccg gca tta ctc<br>Thr Glu Leu Asp Ile Arg Met Ala Leu Ser Ala Thr Pro Ala Leu Leu<br>            240                 245                 250 | 1085 |
| gca cag cag caa aag gat tac cag act gtc att gct gca tgc aag act<br>Ala Gln Gln Gln Lys Asp Tyr Gln Thr Val Ile Ala Ala Cys Lys Thr<br>            255                 260                 265 | 1133 |
| gtg tca ggc tgc gtg ggc gtc acc ctt tgg gat ttc acg gac aaa gtt c<br>Val Ser Gly Cys Val Gly Val Thr Leu Trp Asp Phe Thr Asp Lys Val<br>            270                 275                 280 | 1182 |
| gtcgcatgac agtcaatatt tcggacttca tcaatctgat tcctgcttaa cgaagtattc | 1242 |
| ttgag cc ccg gga acg ttc gca ggg cag ggg gaa gct tgc ccc tgg atc<br>      Pro Pro Gly Thr Phe Ala Gly Gln Gly Glu Ala Cys Pro Trp Ile<br>      285                 290                 295 | 1291 |

-continued

```
agc tgc gtgaatagcg caggaatact gttccatcca actgatgtcg tatgtgattt    1347
Ser Cys
    300 acag aat att gcc cgg aag tta gcc tat aac ggt atc att tct ggc ttc    1396
     Asn Ile Ala Arg Lys Leu Ala Tyr Asn Gly Ile Ile Ser Gly Phe
             305                 310                 315 gca tga                                                               1402
Ala
```

<210> SEQ ID NO 4
<211> LENGTH: 335
<212> TYPE: PRT
<213> ORGANISM: Hohenbuehelia mastrucata

<400> SEQUENCE: 4

```
Met Lys Leu Val Pro Val Leu Ile Ala Ile Ser Ala Thr Leu Ala Ala
            -15                 -10                  -5

Ala Gln Ala Gly Leu Asn Lys Val Ala Lys Ala Ala Gly Lys Lys Tyr
     -1   1               5                  10

Phe Gly Thr Ala Thr Asn Asn Asn Glu Phe Thr Asp Ala Ser Tyr Phe
 15                  20                  25

Pro Val Leu Asn Asn Val Thr Asp Phe Gly Gln Ile Thr Ala Ala Ile
 30                  35                  40                  45

Ser Met Lys Trp Asp Ala Thr Glu Pro Ser Arg Gly Thr Phe Thr Phe
                 50                  55                  60

Ala Gln Gly Asn Glu Ile Ala Ala Leu Ala Ile Lys Asn Gly Gln Leu
             65                  70                  75

Leu Arg Gly His Asn Cys Val Trp His Gln Gln Leu Pro Ser Trp Val
             80                  85                  90

Thr Ser Gly Asn Phe Asp Val Pro Thr Leu Pro Ser Ile Val Ser Ser
         95                 100                 105

His Cys Leu Pro Leu Trp Asp Ala Ile Glu Gly Leu Val Cys Met Tyr
110                 115                 120                 125

Ser Trp Asp Val Ile Asn Glu Cys Leu Arg Asp Asp Gly Thr Phe Arg
                130                 135                 140

Ser Asp Val Phe Ser Arg Thr Leu Gly Thr Ser Tyr Ile Ala Thr Ala
            145                 150                 155

Leu Arg Ala Ala Arg Ala Ala Asp Pro Thr Ala Lys Leu Tyr Ile Ser
        160                 165                 170

Asp Phe Asn Ile Glu Gly Thr Gly Ala Lys Ser Thr Ala Met Val Asn
    175                 180                 185

Leu Val Lys Phe Leu Gln Ser Gln Gly Val Pro Ile Asp Gly Ile Gly
190                 195                 200                 205

Ile Gln Ala His Leu Ile Val Gly Lys Val Arg Ser Thr Leu Val Ala
                210                 215                 220

Asn Met Arg Gln Phe Thr Ala Leu Gly Val Glu Ile Ala Phe Thr Glu
            225                 230                 235

Leu Asp Ile Arg Met Ala Leu Ser Ala Thr Pro Ala Leu Leu Ala Gln
        240                 245                 250

Gln Gln Lys Asp Tyr Gln Thr Val Ile Ala Ala Cys Lys Thr Val Ser
    255                 260                 265

Gly Cys Val Gly Val Thr Leu Trp Asp Phe Thr Asp Lys Val Pro Pro
270                 275                 280                 285

Gly Thr Phe Ala Gly Gln Gly Glu Ala Cys Pro Trp Ile Ser Cys Asn
                290                 295                 300
```

```
                  Ile Ala Arg Lys Leu Ala Tyr Asn Gly Ile Ile Ser Gly Phe Ala
                              305                 310                 315

<210> SEQ ID NO 5
<211> LENGTH: 1768
<212> TYPE: DNA
<213> ORGANISM: Hohenbuehelia mastrucata
<220> FEATURE:
<221> NAME/KEY: CDS
<222> LOCATION: (1)..(85)
<220> FEATURE:
<221> NAME/KEY: sig_peptide
<222> LOCATION: (1)..(63)
<220> FEATURE:
<221> NAME/KEY: mat_peptide
<222> LOCATION: (64)..()
<220> FEATURE:
<221> NAME/KEY: Intron
<222> LOCATION: (86)..(138)
<220> FEATURE:
<221> NAME/KEY: CDS
<222> LOCATION: (139)..(233)
<220> FEATURE:
<221> NAME/KEY: Intron
<222> LOCATION: (234)..(317)
<220> FEATURE:
<221> NAME/KEY: CDS
<222> LOCATION: (318)..(563)
<220> FEATURE:
<221> NAME/KEY: Intron
<222> LOCATION: (564)..(621)
<220> FEATURE:
<221> NAME/KEY: CDS
<222> LOCATION: (622)..(746)
<220> FEATURE:
<221> NAME/KEY: Intron
<222> LOCATION: (747)..(799)
<220> FEATURE:
<221> NAME/KEY: CDS
<222> LOCATION: (800)..(892)
<220> FEATURE:
<221> NAME/KEY: Intron
<222> LOCATION: (893)..(945)
<220> FEATURE:
<221> NAME/KEY: CDS
<222> LOCATION: (946)..(947)
<220> FEATURE:
<221> NAME/KEY: Intron
<222> LOCATION: (948)..(1009)
<220> FEATURE:
<221> NAME/KEY: CDS
<222> LOCATION: (1010)..(1030)
<220> FEATURE:
<221> NAME/KEY: Intron
<222> LOCATION: (1031)..(1086)
<220> FEATURE:
<221> NAME/KEY: CDS
<222> LOCATION: (1087)..(1538)
<220> FEATURE:
<221> NAME/KEY: Intron
<222> LOCATION: (1539)..(1602)
<220> FEATURE:
<221> NAME/KEY: CDS
<222> LOCATION: (1603)..(1659)
<220> FEATURE:
<221> NAME/KEY: Intron
<222> LOCATION: (1660)..(1714)
<220> FEATURE:
<221> NAME/KEY: CDS
<222> LOCATION: (1715)..(1765)

<400> SEQUENCE: 5 atg acg gtc aag gct act ctc gcc ttc agc gcg ctg ctc tct ctt cta    48
Met Thr Val Lys Ala Thr Leu Ala Phe Ser Ala Leu Leu Ser Leu Leu
    -20                 -15                 -10 cct ttc gcc gtc gca cag tcc ggc cct tgg ggg caa t gttcgtcgcc      95
Pro Phe Ala Val Ala Gln Ser Gly Pro Trp Gly Gln
```

-continued

```
      -5           -1  1              5
catttgtac cagtttttat acgcaatact gagctgttct tag gt ggt gga acg      149
                                              Cys Gly Gly Thr
                                                           10 ggt tgg act ggt gct act acc tgc gtt gct ggt tgg act tgc atg tat   197
Gly Trp Thr Gly Ala Thr Thr Cys Val Ala Gly Trp Thr Cys Met Tyr
            15                  20                  25 agc aat ccg tgg tac tcc cag tgt ctt caa ggc gcg gtgagcgcat        243
Ser Asn Pro Trp Tyr Ser Gln Cys Leu Gln Gly Ala
        30                  35 ccctcctttt ttaagctgag cctactcgta tcgccacacg atgtttctga caaactttcg 303 ttattgaacg ccag gct tcc agc acg tcc gga acg ccc agc tcc agc tcc  353
                Ala Ser Ser Thr Ser Gly Thr Pro Ser Ser Ser Ser
                    40                  45                  50 agc tcg tct agt tct agc aca gtt tcc agc tct act gct cta cca acc  401
Ser Ser Ser Ser Ser Ser Thr Val Ser Ser Ser Thr Ala Leu Pro Thr
            55                  60                  65 gcc aca tcc tca gct ggc ctt cat aca gtt gcc aaa gcc aag ggc aaa  449
Ala Thr Ser Ser Ala Gly Leu His Thr Val Ala Lys Ala Lys Gly Lys
            70                  75                  80 ctc tac ttt ggt tcg gca acc gat aac ccc gag ctt tct gac gcg acc  497
Leu Tyr Phe Gly Ser Ala Thr Asp Asn Pro Glu Leu Ser Asp Ala Thr
            85                  90                  95 tac aag gct gga ctt agc aac acc atg gag ttt ggc cag att acg cct  545
Tyr Lys Ala Gly Leu Ser Asn Thr Met Glu Phe Gly Gln Ile Thr Pro
100             105                 110                 115 ggg aac agc atg aaa tgg gtgcgtattg catgggtctg ttgtggttac          593
Gly Asn Ser Met Lys Trp
                120 tcaagcgcga gacctgaagg ataactag gac gca acc gag ccc agc cgc gga   645
                              Asp Ala Thr Glu Pro Ser Arg Gly
                                              125 aca ttc acg ttc acg aac ggt gac gtt att gcc aac ctg gcg gct gca  693
Thr Phe Thr Phe Thr Asn Gly Asp Val Ile Ala Asn Leu Ala Ala Ala
130             135                 140                 145 aac ggc cag ctt ctg cga ggc gcg cat tta cga ttt ctt aat ctc gta  741
Asn Gly Gln Leu Leu Arg Gly Ala His Leu Arg Phe Leu Asn Leu Val
            150                 155                 160 gtg at  gtattcaaaa gcattctagg ccacaattgt gtctggcaca gtcaactccc    796
Val Ile tag c tgg gtg acc gcc ggt aac ttc aac gcc acc gag ctc acg agc atc 845
      Trp Val Thr Ala Gly Asn Phe Asn Ala Thr Glu Leu Thr Ser Ile
          165                 170                 175 gtc cag act cac tgc agc act gtc gtc ggc cat tac aag ggc aaa gc   892
Val Gln Thr His Cys Ser Thr Val Val Gly His Tyr Lys Gly Lys Ala
    180                 185                 190 gtgagttttc tcattgtatc acatcgtttc tttgactaac gagtcatttg cag t t    947 gtaagtacta agctcctgga tacacaaaca agataaacca cttatgttta aatctccttc 1007 ag at  tca tgg gac gtt gtg aac g gtaagatttg taaactcatt ggcagcattc 1060
       Tyr Ser Trp Asp Val Val Asn
       195                 200 tttatttaat gacgatcaaa ttatag ag ccc ttc aat gac gac ggc aca ttc  1112
                               Glu Pro Phe Asn Asp Asp Gly Thr Phe
                                              205                 210 cgc acc tcc gtc ttc tac acc acg ctc ggc aca gac tac att gcc acc  1160
Arg Thr Ser Val Phe Tyr Thr Thr Leu Gly Thr Asp Tyr Ile Ala Thr
            215                 220                 225 gcg ctc aag gcc gcg cgc gcc gcg gac ccg gac aca aag ctg tac atc  1208
```

```
                Ala Leu Lys Ala Ala Arg Ala Ala Asp Pro Asp Thr Lys Leu Tyr Ile
                            230                 235                 240 aac gac tac aac atc gac ggc acc ggc gcc aag tcg acc gcg atg gtc        1256
Asn Asp Tyr Asn Ile Asp Gly Thr Gly Ala Lys Ser Thr Ala Met Val
            245                 250                 255 aac ctc gtg aca cag ctc aag gca gct ggt gtg ccc att gac ggt atc        1304
Asn Leu Val Thr Gln Leu Lys Ala Ala Gly Val Pro Ile Asp Gly Ile
        260                 265                 270 ggc atc caa ggg cat ctc atc gtc ggc gcc gtg cct tcg act atc cag        1352
Gly Ile Gln Gly His Leu Ile Val Gly Ala Val Pro Ser Thr Ile Gln
275                 280                 285                 290 gcc aac atc gag cag ttc gcg gca ctc ggc gtc gag gtc gcc atc acc        1400
Ala Asn Ile Glu Gln Phe Ala Ala Leu Gly Val Glu Val Ala Ile Thr
                295                 300                 305 gag ctc gac atc cgc atg aca ctc cca gtg acg ccc gag aag ctc gcg        1448
Glu Leu Asp Ile Arg Met Thr Leu Pro Val Thr Pro Glu Lys Leu Ala
            310                 315                 320 cag cag aaa acg gac tac cag aac gtg atc aag gcg tgc aat gcc gtc        1496
Gln Gln Lys Thr Asp Tyr Gln Asn Val Ile Lys Ala Cys Asn Ala Val
        325                 330                 335 ccc aag tgc atc ggc gtt acg att tgg gat tac act gat aag                1538
Pro Lys Cys Ile Gly Val Thr Ile Trp Asp Tyr Thr Asp Lys
    340                 345                 350 gtgcggtgct gaatcttttc gcttcttcgg cgacgtgcgg cctgaccttt tgtgtacccg      1598 atag tac tcg tgg att ccc agc gtg ttc agc gga cag ggc gct gcg ctc       1647
     Tyr Ser Trp Ile Pro Ser Val Phe Ser Gly Gln Gly Ala Ala Leu
                 355                 360                 365 cct tgg gac gag gtgtgttctc cgttaatcga tctttacttt cctgattttg            1699
Pro Trp Asp Glu
        370 acccgaatct cccag aac tac gtc aag aag ccc gct tat gac ggt att gtc       1750
             Asn Tyr Val Lys Lys Pro Ala Tyr Asp Gly Ile Val
                             375                 380 acc ggc ttc ggc gta tga                                                1768
Thr Gly Phe Gly Val
    385

<210> SEQ ID NO 6
<211> LENGTH: 409
<212> TYPE: PRT
<213> ORGANISM: Hohenbuehelia mastrucata

<400> SEQUENCE: 6

Met Thr Val Lys Ala Thr Leu Ala Phe Ser Ala Leu Ser Leu Leu
        -20                 -15                 -10

Pro Phe Ala Val Ala Gln Ser Gly Pro Trp Gly Gln Cys Gly Gly Thr
-5                  -1  1               5                   10

Gly Trp Thr Gly Ala Thr Thr Cys Val Ala Gly Trp Thr Cys Met Tyr
            15                  20                  25

Ser Asn Pro Trp Tyr Ser Gln Cys Leu Gln Gly Ala Ala Ser Ser Thr
        30                  35                  40

Ser Gly Thr Pro Ser Ser Ser Ser Ser Ser Ser Ser Thr Val
    45                  50                  55

Ser Ser Ser Thr Ala Leu Pro Thr Ala Thr Ser Ser Ala Gly Leu His
60                  65                  70                  75

Thr Val Ala Lys Ala Lys Gly Lys Leu Tyr Phe Gly Ser Ala Thr Asp
            80                  85                  90

Asn Pro Glu Leu Ser Asp Ala Thr Tyr Lys Ala Gly Leu Ser Asn Thr
        95                  100                 105
```

```
Met Glu Phe Gly Gln Ile Thr Pro Gly Asn Ser Met Lys Trp Asp Ala
            110                 115                 120

Thr Glu Pro Ser Arg Gly Thr Phe Thr Phe Thr Asn Gly Asp Val Ile
        125                 130                 135

Ala Asn Leu Ala Ala Asn Gly Gln Leu Leu Arg Gly Ala His Leu
140                 145                 150                 155

Arg Phe Leu Asn Leu Val Val Ile Trp Val Thr Ala Gly Asn Phe Asn
                160                 165                 170

Ala Thr Glu Leu Thr Ser Ile Val Gln Thr His Cys Ser Thr Val Val
            175                 180                 185

Gly His Tyr Lys Gly Lys Ala Tyr Ser Trp Asp Val Asn Glu Pro
        190                 195                 200

Phe Asn Asp Asp Gly Thr Phe Arg Thr Ser Val Phe Tyr Thr Thr Leu
    205                 210                 215

Gly Thr Asp Tyr Ile Ala Thr Ala Leu Lys Ala Ala Arg Ala Ala Asp
220                 225                 230                 235

Pro Asp Thr Lys Leu Tyr Ile Asn Asp Tyr Asn Ile Asp Gly Thr Gly
                240                 245                 250

Ala Lys Ser Thr Ala Met Val Asn Leu Val Thr Gln Leu Lys Ala Ala
            255                 260                 265

Gly Val Pro Ile Asp Gly Ile Gly Ile Gln Gly His Leu Ile Val Gly
        270                 275                 280

Ala Val Pro Ser Thr Ile Gln Ala Asn Ile Glu Gln Phe Ala Ala Leu
    285                 290                 295

Gly Val Glu Val Ala Ile Thr Glu Leu Asp Ile Arg Met Thr Leu Pro
300                 305                 310                 315

Val Thr Pro Glu Lys Leu Ala Gln Gln Lys Thr Asp Tyr Gln Asn Val
                320                 325                 330

Ile Lys Ala Cys Asn Ala Val Pro Lys Cys Ile Gly Val Thr Ile Trp
            335                 340                 345

Asp Tyr Thr Asp Lys Tyr Ser Trp Ile Pro Ser Val Phe Ser Gly Gln
        350                 355                 360

Gly Ala Ala Leu Pro Trp Asp Glu Asn Tyr Val Lys Lys Pro Ala Tyr
    365                 370                 375

Asp Gly Ile Val Thr Gly Phe Gly Val
380                 385

<210> SEQ ID NO 7
<211> LENGTH: 2169
<212> TYPE: DNA
<213> ORGANISM: Hohenbuehelia mastrucata
<220> FEATURE:
<221> NAME/KEY: CDS
<222> LOCATION: (1)..(79)
<220> FEATURE:
<221> NAME/KEY: sig_peptide
<222> LOCATION: (1)..(60)
<220> FEATURE:
<221> NAME/KEY: mat_peptide
<222> LOCATION: (61)..()
<220> FEATURE:
<221> NAME/KEY: Intron
<222> LOCATION: (80)..(144)
<220> FEATURE:
<221> NAME/KEY: CDS
<222> LOCATION: (145)..(170)
<220> FEATURE:
<221> NAME/KEY: Intron
<222> LOCATION: (171)..(225)
<220> FEATURE:
<221> NAME/KEY: CDS
```

```
<222> LOCATION: (226)..(232)
<220> FEATURE:
<221> NAME/KEY: Intron
<222> LOCATION: (233)..(289)
<220> FEATURE:
<221> NAME/KEY: CDS
<222> LOCATION: (290)..(335)
<220> FEATURE:
<221> NAME/KEY: Intron
<222> LOCATION: (336)..(391)
<220> FEATURE:
<221> NAME/KEY: CDS
<222> LOCATION: (392)..(573)
<220> FEATURE:
<221> NAME/KEY: Intron
<222> LOCATION: (574)..(647)
<220> FEATURE:
<221> NAME/KEY: CDS
<222> LOCATION: (648)..(706)
<220> FEATURE:
<221> NAME/KEY: Intron
<222> LOCATION: (707)..(763)
<220> FEATURE:
<221> NAME/KEY: CDS
<222> LOCATION: (764)..(779)
<220> FEATURE:
<221> NAME/KEY: Intron
<222> LOCATION: (780)..(840)
<220> FEATURE:
<221> NAME/KEY: CDS
<222> LOCATION: (841)..(930)
<220> FEATURE:
<221> NAME/KEY: Intron
<222> LOCATION: (931)..(982)
<220> FEATURE:
<221> NAME/KEY: CDS
<222> LOCATION: (983)..(1038)
<220> FEATURE:
<221> NAME/KEY: Intron
<222> LOCATION: (1039)..(1096)
<220> FEATURE:
<221> NAME/KEY: CDS
<222> LOCATION: (1097)..(1157)
<220> FEATURE:
<221> NAME/KEY: Intron
<222> LOCATION: (1158)..(1220)
<220> FEATURE:
<221> NAME/KEY: CDS
<222> LOCATION: (1221)..(1240)
<220> FEATURE:
<221> NAME/KEY: Intron
<222> LOCATION: (1241)..(1278)
<220> FEATURE:
<221> NAME/KEY: CDS
<222> LOCATION: (1279)..(1292)
<220> FEATURE:
<221> NAME/KEY: Intron
<222> LOCATION: (1293)..(1345)
<220> FEATURE:
<221> NAME/KEY: CDS
<222> LOCATION: (1346)..(1406)
<220> FEATURE:
<221> NAME/KEY: Intron
<222> LOCATION: (1407)..(1471)
<220> FEATURE:
<221> NAME/KEY: CDS
<222> LOCATION: (1472)..(1524)
<220> FEATURE:
<221> NAME/KEY: Intron
<222> LOCATION: (1525)..(1584)
<220> FEATURE:
<221> NAME/KEY: CDS
<222> LOCATION: (1585)..(1634)
<220> FEATURE:
<221> NAME/KEY: Intron
<222> LOCATION: (1635)..(1692)
<220> FEATURE:
<221> NAME/KEY: CDS
<222> LOCATION: (1693)..(1772)
<220> FEATURE:
```

```
<221> NAME/KEY: Intron
<222> LOCATION: (1773)..(1832)
<220> FEATURE:
<221> NAME/KEY: CDS
<222> LOCATION: (1833)..(2015)
<220> FEATURE:
<221> NAME/KEY: Intron
<222> LOCATION: (2016)..(2076)
<220> FEATURE:
<221> NAME/KEY: CDS
<222> LOCATION: (2077)..(2163)

<400> SEQUENCE: 7 atg atg gtc aag ttg tct ctt act gtc tta gtc gct gtc gtc gct ggt       48
Met Met Val Lys Leu Ser Leu Thr Val Leu Val Ala Val Val Ala Gly
-20             -15                 -10                 -5 cgt gtt tcg gcc gtc cct gtt tgg ggc caa t gtcagtgaga tcatcgatca       99
Arg Val Ser Ala Val Pro Val Trp Gly Gln
        -1   1               5 tcgctgatgt atagctcgga ctattaaccg tgcaccttat tgtag gc  ggt ggt ctg     155
                                                     Cys Gly Gly Leu
                                                                 10 aat tgg act ggc ggc gtacgttcat tttcaataag tattgcccac gttagctgac      210
Asn Trp Thr Gly Gly
                15 ttgttacttc ttcag aca aca t gtacgtcaaa ttgtatgaag ttcagtaagt          262
               Thr Thr agatccgttg accagactta cattcag gc  gat acc gga tcc acc tgt gtt aag    315
                                 Cys Asp Thr Gly Ser Thr Cys Val Lys
                                                 20                 25 cag aac gac tgg tac tct ca  gttagtcctg cgatgcgttc tcgctctata         365
Gln Asn Asp Trp Tyr Ser Gln
             30 taattcctaa acgagatgtt atacag a tgc ttg cct ggt aca caa cca cag       416
                               Cys Leu Pro Gly Thr Gln Pro Gln
                                         35                 40 ccg aca ccc act ccg acg act cca aca tcg acg gtt ggc cca acg acc      464
Pro Thr Pro Thr Pro Thr Thr Pro Thr Ser Thr Val Gly Pro Thr Thr
             45                  50                  55 act ccc act ccc act agc ggc tcc ggc tcc ggc ctc gat act cac ttc      512
Thr Pro Thr Pro Thr Ser Gly Ser Gly Ser Gly Leu Asp Thr His Phe
             60                  65                  70 aag gct aag gga aag aaa ttc tgg ggc tct tgc gct gat cca ggc aca      560
Lys Ala Lys Gly Lys Lys Phe Trp Gly Ser Cys Ala Asp Pro Gly Thr
             75                  80                  85 ttg aac atc gcc g gtatgttgct cgcatgatgc gggactccta aaagtttatc        613
Leu Asn Ile Ala
90 gttgatctgg gattgatctg ggattatcct atag ca  aat gcc aat gtc ctg aag    667
                                         Ala Asn Ala Asn Val Leu Lys
                                                     95             100 gca gag ttc ggt cag gta acg ccg gag aac tct atg aag gtacgaattc       716
Ala Glu Phe Gly Gln Val Thr Pro Glu Asn Ser Met Lys
             105                 110 caatcccaac atctcaagat tgggctcaaa tatcccctta tacttag tgg gac gct      772
                                                     Trp Asp Ala
                                                             115 acc gaa c gtgtgttatc actacatttc attcgctgaa ctgacatctt gacgagggtc    829
Thr Glu acgactcaca g cc  agc cgc aac caa ttc aac ttt ggc aat gct gat acg     878
              Pro Ser Arg Asn Gln Phe Asn Phe Gly Asn Ala Asp Thr
                      120                 125                 130
```

| | |
|---|---|
| ctc gtc aac tgg gct atc tca aac ggc aaa ctg atc cgc ggt cac act<br>Leu Val Asn Trp Ala Ile Ser Asn Gly Lys Leu Ile Arg Gly His Thr<br>              135                140              145 | 926 |
| ttg g gtacagtcaa tattttctct taccgtgctc tctcattgac ggtatcctct ag<br>Leu | 982 |
| tc tgg cat tca cag ctg ccg ggc tgg gtt tcg gcc atc aac gat aag<br>Val Trp His Ser Gln Leu Pro Gly Trp Val Ser Ala Ile Asn Asp Lys<br>      150              155              160 | 1029 |
| acc act ttg gtttgtcact ttgtattttc acgcgtagcg gcattttgat<br>Thr Thr Leu<br>165 | 1078 |
| tgattgcatc gattacag acc tcc gtc atc caa aac cac atc tcc aat ctt<br>                        Thr Ser Val Ile Gln Asn His Ile Ser Asn Leu<br>                                    170              175 | 1129 |
| gct gga aga tac gca ggc aaa ctt tac g gttagtcatg tctgtttcct<br>Ala Gly Arg Tyr Ala Gly Lys Leu Tyr<br>      180              185 | 1177 |
| tgaacattaa cggacactca tgtaagtgat ttttggcatc tag ct gta agc att<br>                                                          Ala Val Ser Ile<br>                                                                    190 | 1231 |
| cac cca aac gtacgctctt ctggtcctga cgcttttcac ttccacag tgg gac gtc<br>His Pro Asn                                                          Trp Asp Val<br>                                                                            195 | 1287 |
| gtc aa gtaagtcgct cccttcgac catgcgaatc cacggcctat gatactcttt<br>Val Asn | 1342 |
| tag t gaa ata ttc aac gag gat ggc tcc ctt cgc tcc agt gtc ttc tcc<br>        Glu Ile Phe Asn Glu Asp Gly Ser Leu Arg Ser Ser Val Phe Ser<br>              200                205                210 | 1391 |
| aac gtc ctc ggc gag gtactctacc ccgtcaatag atctatttc cacgcttta<br>Asn Val Leu Gly Glu<br>215 | 1446 |
| ctgacaatgg aaaacctgaa tgtag tcc ttc gtc act atc gcc ttc caa gct<br>                                          Ser Phe Val Thr Ile Ala Phe Gln Ala<br>                                                    220                225 | 1498 |
| gca aag gcc gcc gat cct agc gcc aa gttagtgaaa ctctcagtac<br>Ala Lys Ala Ala Asp Pro Ser Ala Lys<br>      230                235 | 1544 |
| gataagtaga gatcagcgcc gatgatttat gtacttacag g cgc tac atc aat gac<br>                                                          Arg Tyr Ile Asn Asp<br>                                                                     240 | 1600 |
| tac aat cta gac tca aac aat gca aaa gtt caa g gttagccatt<br>Tyr Asn Leu Asp Ser Asn Asn Ala Lys Val Gln<br>      245                        250 | 1644 |
| tacactgtgc gccgagccga tgcccggggg tctaacttct ggctgcag gt ctg gtt<br>                                                                              Gly Leu Val<br>                                                                                 255 | 1700 |
| gcc ctt gtg aag cgc gtc aac agc gcc aac gcg gac ctc atc cag ggc<br>Ala Leu Val Lys Arg Val Asn Ser Ala Asn Ala Asp Leu Ile Gln Gly<br>      260                        265                        270 | 1748 |
| att ggc acg cag atg cac ctt agt gtacgtgtcc cccttcttgc gcccacgacg<br>Ile Gly Thr Gln Met His Leu Ser<br>      275                        280 | 1802 |
| gaacttctga atccacgcac ttcataatag gcc ggc ggt gtt ggc ggt gtc caa<br>                                                  Ala Gly Gly Val Gly Gly Val Gln<br>                                                                             285 | 1856 |
| gct gcc ctg acc gcc ctc gct ggt gct ggt gtg tcc gaa gtc gca atc<br>Ala Ala Leu Thr Ala Leu Ala Gly Ala Gly Val Ser Glu Val Ala Ile<br>      290                        295                        300 | 1904 |
| acc gag ctc gac atc gtc aac gct gcg cca aac gac tac gtc acc gtt<br>Thr Glu Leu Asp Ile Val Asn Ala Ala Pro Asn Asp Tyr Val Thr Val | 1952 |

```
           305                 310                 315                 320
gcc aag gcc tgc ctc aat acg ccc gct tgc gtg gcg att acg agc tgg       2000
Ala Lys Ala Cys Leu Asn Thr Pro Ala Cys Val Ala Ile Thr Ser Trp
                    325                 330                 335 ggt gtt tcc gac cag gtgcgttgtg cggttttcct ggtttcattt gcactacatc       2055
Gly Val Ser Asp Gln
            340 taacacgcgt tctacgaata g aac tcc tgg cga gcc agt tct acc cct ctc       2106
                        Asn Ser Trp Arg Ala Ser Ser Thr Pro Leu
                                        345                 350 ctg ttt aac aac aac tac cag cct aag ccg gca tac aca gca gtc atc       2154
Leu Phe Asn Asn Asn Tyr Gln Pro Lys Pro Ala Tyr Thr Ala Val Ile
                355                 360                 365 cag gcg ctc gcctga                                                    2169
Gln Ala Leu
        370

<210> SEQ ID NO 8
<211> LENGTH: 390
<212> TYPE: PRT
<213> ORGANISM: Hohenbuehelia mastrucata

<400> SEQUENCE: 8

Met Met Val Lys Leu Ser Leu Thr Val Leu Val Ala Val Val Ala Gly
-20             -15                 -10                  -5

Arg Val Ser Ala Val Pro Val Trp Gly Gln Cys Gly Gly Leu Asn Trp
        -1   1              5                      10

Thr Gly Gly Thr Thr Cys Asp Thr Gly Ser Thr Cys Val Lys Gln Asn
            15                  20                  25

Asp Trp Tyr Ser Gln Cys Leu Pro Gly Thr Gln Pro Gln Pro Thr Pro
        30                  35                  40

Thr Pro Thr Thr Pro Thr Ser Thr Val Gly Pro Thr Thr Thr Pro Thr
45                  50                  55                  60

Pro Thr Ser Gly Ser Gly Ser Gly Leu Asp Thr His Phe Lys Ala Lys
                65                  70                  75

Gly Lys Lys Phe Trp Gly Ser Cys Ala Asp Pro Gly Thr Leu Asn Ile
            80                  85                  90

Ala Ala Asn Ala Asn Val Leu Lys Ala Glu Phe Gly Gln Val Thr Pro
        95                  100                 105

Glu Asn Ser Met Lys Trp Asp Ala Thr Glu Pro Ser Arg Asn Gln Phe
110                 115                 120

Asn Phe Gly Asn Ala Asp Thr Leu Val Asn Trp Ala Ile Ser Asn Gly
125                 130                 135                 140

Lys Leu Ile Arg Gly His Thr Leu Val Trp His Ser Gln Leu Pro Gly
                145                 150                 155

Trp Val Ser Ala Ile Asn Asp Lys Thr Thr Leu Thr Ser Val Ile Gln
            160                 165                 170

Asn His Ile Ser Asn Leu Ala Gly Arg Tyr Ala Gly Lys Leu Tyr Ala
        175                 180                 185

Val Ser Ile His Pro Asn Trp Asp Val Val Asn Glu Ile Phe Asn Glu
    190                 195                 200

Asp Gly Ser Leu Arg Ser Ser Val Phe Ser Asn Val Leu Gly Glu Ser
205                 210                 215                 220

Phe Val Thr Ile Ala Phe Gln Ala Ala Lys Ala Ala Asp Pro Ser Ala
                225                 230                 235

Lys Arg Tyr Ile Asn Asp Tyr Asn Leu Asp Ser Asn Asn Ala Lys Val
            240                 245                 250
```

Gln Gly Leu Val Ala Leu Val Lys Arg Val Asn Ser Ala Asn Ala Asp
        255                 260                 265

Leu Ile Gln Gly Ile Gly Thr Gln Met His Leu Ser Ala Gly Gly Val
    270                 275                 280

Gly Gly Val Gln Ala Ala Leu Thr Ala Leu Ala Gly Ala Gly Val Ser
285                 290                 295                 300

Glu Val Ala Ile Thr Glu Leu Asp Ile Val Asn Ala Ala Pro Asn Asp
                305                 310                 315

Tyr Val Thr Val Ala Lys Ala Cys Leu Asn Thr Pro Ala Cys Val Ala
                320                 325                 330

Ile Thr Ser Trp Gly Val Ser Asp Gln Asn Ser Trp Arg Ala Ser Ser
                335                 340                 345

Thr Pro Leu Leu Phe Asn Asn Asn Tyr Gln Pro Lys Pro Ala Tyr Thr
    350                 355                 360

Ala Val Ile Gln Ala Leu
365                 370

<210> SEQ ID NO 9
<211> LENGTH: 2133
<212> TYPE: DNA
<213> ORGANISM: Hohenbuehelia mastrucata
<220> FEATURE:
<221> NAME/KEY: CDS
<222> LOCATION: (1)..(76)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (77)..(131)
<220> FEATURE:
<221> NAME/KEY: CDS
<222> LOCATION: (132)..(157)
<220> FEATURE:
<221> NAME/KEY: Intron
<222> LOCATION: (158)..(223)
<220> FEATURE:
<221> NAME/KEY: CDS
<222> LOCATION: (224)..(230)
<220> FEATURE:
<221> NAME/KEY: Intron
<222> LOCATION: (231)..(290)
<220> FEATURE:
<221> NAME/KEY: CDS
<222> LOCATION: (291)..(336)
<220> FEATURE:
<221> NAME/KEY: Intron
<222> LOCATION: (337)..(383)
<220> FEATURE:
<221> NAME/KEY: CDS
<222> LOCATION: (384)..(553)
<220> FEATURE:
<221> NAME/KEY: Intron
<222> LOCATION: (554)..(615)
<220> FEATURE:
<221> NAME/KEY: CDS
<222> LOCATION: (616)..(674)
<220> FEATURE:
<221> NAME/KEY: Intron
<222> LOCATION: (675)..(726)
<220> FEATURE:
<221> NAME/KEY: CDS
<222> LOCATION: (727)..(742)
<220> FEATURE:
<221> NAME/KEY: Intron
<222> LOCATION: (743)..(804)
<220> FEATURE:
<221> NAME/KEY: CDS

```
<222> LOCATION: (805)..(894)
<220> FEATURE:
<221> NAME/KEY: Intron
<222> LOCATION: (895)..(952)
<220> FEATURE:
<221> NAME/KEY: CDS
<222> LOCATION: (953)..(1008)
<220> FEATURE:
<221> NAME/KEY: Intron
<222> LOCATION: (1009)..(1056)
<220> FEATURE:
<221> NAME/KEY: CDS
<222> LOCATION: (1057)..(1117)
<220> FEATURE:
<221> NAME/KEY: Intron
<222> LOCATION: (1118)..(1152)
<220> FEATURE:
<221> NAME/KEY: CDS
<222> LOCATION: (1153)..(1172)
<220> FEATURE:
<221> NAME/KEY: Intron
<222> LOCATION: (1173)..(1233)
<220> FEATURE:
<221> NAME/KEY: CDS
<222> LOCATION: (1234)..(1247)
<220> FEATURE:
<221> NAME/KEY: Intron
<222> LOCATION: (1248)..(1308)
<220> FEATURE:
<221> NAME/KEY: CDS
<222> LOCATION: (1309)..(1369)
<220> FEATURE:
<221> NAME/KEY: Intron
<222> LOCATION: (1370)..(1425)
<220> FEATURE:
<221> NAME/KEY: CDS
<222> LOCATION: (1426)..(1478)
<220> FEATURE:
<221> NAME/KEY: Intron
<222> LOCATION: (1479)..(1533)
<220> FEATURE:
<221> NAME/KEY: CDS
<222> LOCATION: (1534)..(1583)
<220> FEATURE:
<221> NAME/KEY: Intron
<222> LOCATION: (1584)..(1644)
<220> FEATURE:
<221> NAME/KEY: CDS
<222> LOCATION: (1645)..(1721)
<220> FEATURE:
<221> NAME/KEY: Intron
<222> LOCATION: (1722)..(1780)
<220> FEATURE:
<221> NAME/KEY: CDS
<222> LOCATION: (1781)..(1963)
<220> FEATURE:
<221> NAME/KEY: Intron
<222> LOCATION: (1964)..(2040)
<220> FEATURE:
<221> NAME/KEY: CDS
<222> LOCATION: (2041)..(2127)

<400> SEQUENCE: 9 atg ttt aaa ttg ctt tct gtg gtc tct ctt gcc att gtt gca ggc cgt      48
Met Phe Lys Leu Leu Ser Val Val Ser Leu Ala Ile Val Ala Gly Arg
                -15                 -10                  -5 gtc agc gct gtc ccc gtc tgg ggt caa t gtgagtatgc tacttcttct          96
Val Ser Ala Val Pro Val Trp Gly Gln
        -1  1               5 gtcctgtgat caaaacctga tatccgagtt gttag gt  ggt ggc atc ggt tgg      148
                                          Cys Gly Gly Ile Gly Trp
                                                              10 acc ggc gga gtaggtgcct ttcacgacgt tttgtgatgg ctctctgacc              197
Thr Gly Gly
        15
```

```
acagctgatt tactcgatga tttcag act aca t gtaagttttg cctatcattt      250
                              Thr Thr gactctattc gccatcaatt gaagagtcat tatgatccag gt  gat gct gga acc   304
                                                Cys Asp Ala Gly Thr
                                                              20 acc tgc atc aaa ttg aat gac tac tat tct ca gtgagtttcc ctaaaatatt  356
Thr Cys Ile Lys Leu Asn Asp Tyr Tyr Ser Gln
            25                  30 taacaaaatc cctctcaatt gttgcag g tgc cag ccc ggt gca tcg gcg ccc   408
                                Cys Gln Pro Gly Ala Ser Ala Pro
                                        35                  40 cct cca acc tcg gtg ccg ccc ccg ccg aca acc agt gtg cct tcc       456
Pro Pro Thr Ser Val Pro Pro Pro Pro Thr Thr Ser Val Pro Ser
            45                  50                  55 ggt cct act cct act ggt gga ctc aac agc cat ttc gtc gca cac gga   504
Gly Pro Thr Pro Thr Gly Gly Leu Asn Ser His Phe Val Ala His Gly
            60                  65                  70 aag aag ttc tgg ggc tcc tgc gct gac tct aat acc ctc aat att gct g 553
Lys Lys Phe Trp Gly Ser Cys Ala Asp Ser Asn Thr Leu Asn Ile Ala
        75                  80                  85 gtaaattaca ctgaaggcct ttggctcagg tttaaagtgt tgaaggtttt tatatttcac  613 ag cc  aac gcc gcc gtg ttg aag tct gac ttc ggt gct gtc act cct    659
       Ala Asn Ala Ala Val Leu Lys Ser Asp Phe Gly Ala Val Thr Pro
           90                  95                  100 gaa aac tcg atg aag gtacgttttc agcatggctg tactcaaaac cttactcaca   714
Glu Asn Ser Met Lys
105 cgtttatctc ag tgg gat gca act gaa c gtacgtaaat tgtggcttgg          762
               Trp Asp Ala Thr Glu
                    110 attcactctt ccaggtttat tgagccgcgc tgcatttgtc ag cc  tcg cga ggt     815
                                                  Pro Ser Arg Gly
                                                            115 cag ttc tcg tac tcc ggc gct gac gca ctc gtc aac tgg gcc gtg tcc   863
Gln Phe Ser Tyr Ser Gly Ala Asp Ala Leu Val Asn Trp Ala Val Ser
    120                 125                 130 aac ggc aag ctg atc cga gga cac act ctt g gtcagttttcc attgttttcg   914
Asn Gly Lys Leu Ile Arg Gly His Thr Leu
135                 140 cgcctcgtcc tcggatcctt atcgaatgcc ttgcatag ta  tgg cac tcc cag ctc 969
                                             Val Trp His Ser Gln Leu
                                                 145                 150 ccg tca tgg gta tcg gcg att aac gac aag acc acc ttg gtaggttcta   1018
Pro Ser Trp Val Ser Ala Ile Asn Asp Lys Thr Thr Leu
            155                 160 ccattggtcc ataattccgt ctgctcaacc ttgtatag acg tcc gtc atc caa aac 1074
                                          Thr Ser Val Ile Gln Asn
                                                      165 cac atc tcg aac ctt gct ggc aga tac aac gga aaa ctc tat g        1117
His Ile Ser Asn Leu Ala Gly Arg Tyr Asn Gly Lys Leu Tyr
170                 175                 180 gtgagcgctg ttagttagtt gatgtctaca tttag ct  gac tta ata cac gca    1169
                                          Ala Asp Leu Ile His Ala
                                                      185 gct gtaagtcgga tgcgtttaat ttcgccgttg ttttaacaat gctctttgat        1222
Ala
190 tttcctccta g tgg gac gtt tgc aa  gtgagtcaac gtgaagttgt ccttttcttt 1277
             Trp Asp Val Cys Asn
                         195
```

```
tcaaaacaac tgagcatcac cctgtgtcta g c gaa atc ttc aac gaa gat ggt      1330
                                    Glu Ile Phe Asn Glu Asp Gly
                                                        200 acc ctc cgc tcc agc gtc ttc tcc aat gtt ctt ggc gag gtacacttgc       1379
Thr Leu Arg Ser Ser Val Phe Ser Asn Val Leu Gly Glu
            205                 210                 215 tatggctact ttctaattta ggcttaccca tcctttcctt gcgcag tct ttc gtc        1434
                                                Ser Phe Val act att gca ttc caa gct gcg cgc gct gca gac tcc acc gcc aa           1478
Thr Ile Ala Phe Gln Ala Ala Arg Ala Ala Asp Ser Thr Ala Lys
        220                 225                 230 gttcgattgt tctttgatac caaggtttga cctattctta tttggctcac tacag g       1534 ctc tac atc aac gac tac aac ctc gac tcg aac aac gcc aag gtt cag g    1583
Leu Tyr Ile Asn Asp Tyr Asn Leu Asp Ser Asn Asn Ala Lys Val Gln
        235                 240                 245 gtacgttgac agaaatcgga atccatcgag gcccatcatt aattattctg atcgccctca    1643 g gc atg gtc gcc ctc gtc aag cgc gtg aat gcc aac ggc aaa ctc atc     1691
  Gly Met Val Ala Leu Val Lys Arg Val Asn Ala Asn Gly Lys Leu Ile
      250                 255                 260                 265 gac ggt att ggt aca cag atg cac ttg agt gtgcgtcccg cttctatgaa        1741
Asp Gly Ile Gly Thr Gln Met His Leu Ser
                270                 275 ctaaagatct tctccatgtt aacatattct ttcccctag gcc ggt ggt gct ggt       1795
                                            Ala Gly Gly Ala Gly
                                                            280 ggt gcc caa gct gcc ctg acc gcg ctc gct agc tcc ggt gtg ggt gag      1843
Gly Ala Gln Ala Ala Leu Thr Ala Leu Ala Ser Ser Gly Val Gly Glu
            285                 290                 295 atc gcg atc aca gag ctc gac att gtc aac gca tcg ccc aat gac tat      1891
Ile Ala Ile Thr Glu Leu Asp Ile Val Asn Ala Ser Pro Asn Asp Tyr
            300                 305                 310 acc act gtc gtc aat gct tgc ctt aac acg cct gct tgc att tca atc      1939
Thr Thr Val Val Asn Ala Cys Leu Asn Thr Pro Ala Cys Ile Ser Ile
            315                 320                 325 acc agc tgg ggt gtc tcc gat acg gtgcgtgttc acagtcctgc atgatttcgt     1993
Thr Ser Trp Gly Val Ser Asp Thr
            330                 335 ctttccgatc atgtctgtca ctgcgtcctt tcatcgcggt attatag aac tcg tgg      2049
                                                    Asn Ser Trp cgc gca agc tct acc ccg ctc ttg ttc gac ggc aac tac aag ccc aaa      2097
Arg Ala Ser Ser Thr Pro Leu Leu Phe Asp Gly Asn Tyr Lys Pro Lys
340                 345                 350                 355 cca gcg tac acc gcg atc atg caa ctt ctc ggatga                       2133
Pro Ala Tyr Thr Ala Ile Met Gln Leu Leu
                360                 365

<210> SEQ ID NO 10
<211> LENGTH: 384
<212> TYPE: PRT
<213> ORGANISM: Hohenbuehelia mastrucata

<400> SEQUENCE: 10

Met Phe Lys Leu Leu Ser Val Val Ser Leu Ala Ile Val Ala Gly Arg
                -15                 -10                 -5

Val Ser Ala Val Pro Val Trp Gly Gln Cys Gly Gly Ile Gly Trp Thr
            -1  1               5                   10

Gly Gly Thr Thr Cys Asp Ala Gly Thr Thr Cys Ile Lys Leu Asn Asp
        15                  20                  25
```

-continued

```
Tyr Tyr Ser Gln Cys Gln Pro Gly Ala Ser Ala Pro Pro Thr Ser
 30              35              40              45

Val Pro Pro Pro Pro Thr Thr Ser Val Pro Ser Gly Pro Thr Pro
                 50              55              60

Thr Gly Gly Leu Asn Ser His Phe Val Ala His Gly Lys Lys Phe Trp
             65              70              75

Gly Ser Cys Ala Asp Ser Asn Thr Leu Asn Ile Ala Ala Asn Ala Ala
         80              85              90

Val Leu Lys Ser Asp Phe Gly Ala Val Thr Pro Glu Asn Ser Met Lys
     95             100             105

Trp Asp Ala Thr Glu Pro Ser Arg Gly Gln Phe Ser Tyr Ser Gly Ala
110             115             120             125

Asp Ala Leu Val Asn Trp Ala Val Ser Asn Gly Lys Leu Ile Arg Gly
             130             135             140

His Thr Leu Val Trp His Ser Gln Leu Pro Ser Trp Val Ser Ala Ile
             145             150             155

Asn Asp Lys Thr Thr Leu Thr Ser Val Ile Gln Asn His Ile Ser Asn
         160             165             170

Leu Ala Gly Arg Tyr Asn Gly Lys Leu Tyr Ala Asp Leu Ile His Ala
175             180             185

Ala Trp Asp Val Cys Asn Glu Ile Phe Asn Glu Asp Gly Thr Leu Arg
190             195             200             205

Ser Ser Val Phe Ser Asn Val Leu Gly Glu Ser Phe Val Thr Ile Ala
             210             215             220

Phe Gln Ala Ala Arg Ala Ala Asp Ser Thr Ala Lys Leu Tyr Ile Asn
         225             230             235

Asp Tyr Asn Leu Asp Ser Asn Asn Ala Lys Val Gln Gly Met Val Ala
         240             245             250

Leu Val Lys Arg Val Asn Ala Asn Gly Lys Leu Ile Asp Gly Ile Gly
     255             260             265

Thr Gln Met His Leu Ser Ala Gly Gly Ala Gly Gly Ala Gln Ala Ala
270             275             280             285

Leu Thr Ala Leu Ala Ser Ser Gly Val Gly Glu Ile Ala Ile Thr Glu
             290             295             300

Leu Asp Ile Val Asn Ala Ser Pro Asn Asp Tyr Thr Thr Val Val Asn
         305             310             315

Ala Cys Leu Asn Thr Pro Ala Cys Ile Ser Ile Thr Ser Trp Gly Val
         320             325             330

Ser Asp Thr Asn Ser Trp Arg Ala Ser Ser Thr Pro Leu Leu Phe Asp
     335             340             345

Gly Asn Tyr Lys Pro Lys Pro Ala Tyr Thr Ala Ile Met Gln Leu Leu
350             355             360             365
```

POLYPEPTIDES HAVING XYLANASE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having xylanase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Xylanases degrade beta-1,4-xylan into xylose, thus breaking down hemicellulose, one of the major components of plant cell walls.

There is a need in the art to improve cellulolytic and hemicellulolytic enzyme compositions through supplementation with additional enzymes to increase efficiency and to provide cost-effective enzyme solutions for degradation of lignocellulose.

The present invention provides polypeptides having xylanase activity and polynucleotides encoding the polypeptides.

SUMMARY OF THE INVENTION

The present invention relates to isolated polypeptides having xylanase activity selected from the group consisting of:

(a) a polypeptide having at least 68% sequence identity to the mature polypeptide of SEQ ID NO: 2, or a polypeptide having at least 64% sequence identity to the mature polypeptide of SEQ ID NO: 4, or a polypeptide having at least 70% sequence identity to the mature polypeptide of SEQ ID NO: 6, or a polypeptide having at least 74% sequence identity to the mature polypeptide of SEQ ID NO: 8, or a polypeptide having at least 75% sequence identity to the mature polypeptide of SEQ ID NO: 10;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, SEQ ID NO: 5, SEQ ID NO: 7, or SEQ ID NO: 9; or the cDNA sequence thereof;

(d) a variant of the mature polypeptide of SEQ ID NO: 2, SEQ ID NO: 4, SEQ ID NO: 6, SEQ ID NO: 8, or SEQ ID NO: 10 comprising a substitution, deletion, and/or insertion at one or more (e.g., several) positions; and (e) a fragment of the polypeptide of (a), (b), (c), or (d) that has xylanase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 20 to 334 of SEQ ID NO: 2), a catalytic domain having at least 60% sequence identity to the catalytic domain of SEQ ID NO: 4 (for example, amino acids 20 to 335 of SEQ ID NO: 4), a catalytic domain having at least 60% sequence identity to the catalytic domain of SEQ ID NO: 6 (for example, amino acids 95 to 409 of SEQ ID NO: 6), a catalytic domain having at least 60% sequence identity to the catalytic domain of SEQ ID NO: 8 (for example, amino acids 89 to 391 of SEQ ID NO: 8), or a catalytic domain having at least 60% sequence identity to the catalytic domain of SEQ ID NO: 10 (for example, amino acids 84 to 385 of SEQ ID NO: 10);

(b) a catalytic domain encoded by a polynucleotide having at least 60% sequence identity to the catalytic domain coding sequence of SEQ ID NO: 1 (for example, nucleotides 58-204, 255-345, 400-526, 581-582, 645-665, 717-1168, 1232-1288, and 1346-1393 of SEQ ID NO: 1), a catalytic domain encoded by a polynucleotide having at least 60% sequence identity to the catalytic domain coding sequence of SEQ ID NO: 3 (for example, nucleotides 58-204, 267-357, 411-537, 595-602, 656-676, 727-1182, 1248-1297, and 1352-1399 of SEQ ID NO: 3), a catalytic domain encoded by a polynucleotide having at least 60% sequence identity to the catalytic domain coding sequence of SEQ ID NO: 5 (for example, nucleotides 420-563, 622-746, 800-892, 946-947, 1010-1030, 1087-1538, 1603-1659, and 1715-1765 of SEQ ID NO: 5), a catalytic domain encoded by a polynucleotide having at least 60% sequence identity to the catalytic domain coding sequence of SEQ ID NO: 7 (for example, nucleotides 498-573, 648-706, 764-779, 841-930, 983-1038, 1097-1157, 1221-1240, 1279-1292, 1346-1406, 1472-1524, 1585-1634, 1693-1772, 1833-2015, and 2077-2166 of SEQ ID NO: 7), or a catalytic domain encoded by a polynucleotide having at least 60% sequence identity to the catalytic domain coding sequence of SEQ ID NO: 9 (for example, nucleotides 478-553, 616-674, 727-742, 805-894, 953-1008, 1057-1117, 1153-1172, 1234-1247, 1309-1369, 1426-1478, 1534-1583, 1645-1721, 1781-1963, and 2041-2130 of SEQ ID NO: 9);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, or SEQ ID NO: 10; and (d) a fragment of a catalytic domain of (a), (b), or (c), which has xylanase activity.

The present invention also relates to isolated polynucleotides encoding the polypeptides of the present invention; nucleic acid constructs; recombinant expression vectors;

recombinant host cells comprising the polynucleotides; and methods of producing the polypeptides.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The present invention also relates to a polynucleotide encoding a signal peptide comprising or consisting of amino acids 1 to 19 of SEQ ID NO: 2, amino acids 1 to 19 of SEQ ID NO: 4, amino acids 1 to 21 of SEQ ID NO: 6, amino acids 1 to 20 of SEQ ID NO: 8, or amino acids 1 to 19 of SEQ ID NO: 10, which is operably linked to a gene encoding a protein; nucleic acid constructs, expression vectors, and recombinant host cells comprising the polynucleotides; and methods of producing a protein.

SEQUENCES OF THE INVENTION

*Hohenbuehelia mastrucata* Strain NN009379 Genomic Nucleotide Sequence (SEQ ID NO: 1):

```
   1   ATGAAATCCG CCCTCTTGGT CCTCACGGTG ACAGTGCCTT TCGCTGCAGC ACAGGCAGGG TTGAATAGGG TGGCGAAAGC
  81   AGCTGGGAAG CTATACTTTG GGACAGCAAC AAACCTGGAA CAATTCACGG ATGCGCCATA CTTTGCCGTG CTGAACAATG
 161   TCACCGAGTT CGGACAGATC ACTGCCGCAA ATAGCATGAA ATGGGTACGT TCACGCGATT TCGTGCGTAT TATATATGCT
 241   GACTTGCATC AAAGGATGCG ACCGAACCCT CTAGGGGCGT CTTCACCTTC GCTCAAGGAG ATCAAATCGC GGCTCTCGCG
 321   CAGCAGAACG GCCAGCTTCT TAGAGGTCAG TGCCGTATCA TTGAACCAAA CCGAGCGGGG TGATTATCTT CCGCCGCAGG
 401   TCACAATTGT GTCTGGCACC AACAGCTCCC TGCCTGGGTC ACAGACGGAA ACTTTGATGC CCCAACCTTA ACGAGTATTG
 481   TTGAGACTCA TTGCTCAACA ATCGTTGATC ATTACAAAGG CCAAATGTCA GTTAGTTTCC ATGATCGCCG CGACGAATAC
 561   TAAAGAGTAC TTGTTTTCAG ATGTATGACT CACTTGAGAG CCATGTGCAC AGAAACATGC TGATATGATT TTCCTTGACT
 641   TTAGACAGCT GGGATGTCAT CAACGGTGAG CCAGAATGTC GTTGCTGATC AATTACTTTG CTTATACAAT ACTTAGAGTG
 721   CCTGAATGAC GACGGCACGT TCCGCGAGGA TGTCTTCTTC GATACCCTGA ACACCTCGTA CATCGCCACT GCCCTTCGCG
 801   CAGCACGCGC CGCCGACCCA AACGCAAAGC TCTACATAAA CGACTTCAAT ATCGAGGGCA CCGGTCCAAA ATCCACCGCT
 881   ATGGTCAACC TGGTCAAGTC CCTTCAAGCT CAAAACGTGC CGATCGACGG CATTGGCATC CAAACCCACC TCATCGTCGG
 961   CGAGGTCCCA AGCACGCTCC TCGAAAACAT GCAGCAATTC ACGGCGTTGG GCGTGGAGAT CGCTATTACT GAGTTGGATA
1041   TCCGCATGAC CCTTCCCGAT ACGCCAGAGC TGCGTGCTCA ACAACAGCAG GATTACCAGA CTGTCATCGA GGCTTGTAAC
1121   ACAGTGCCCG AATGTGTGGG TGTGACTGTA TGGGATTTCA CCGACAAGGT ACGAGGTGTT CGTTCCTCGA GGAAGCTGCA
1201   GGAGCTAATC TGAGCCGCTG TGTGCCCACA GTATTCGTGG GTCCCAGGTA CTTTCACAGG CCAAGGAGAT GCTTGTCCAT
1281   GGGACGAGGT GGGTGATTGC ACGCCACATC ATTTTGCTGC GAAACTGATG CGAGGCGGCT CTCAGAATAT CGTCAGGAAG
1361   TCAGCGTACG ATGGTATTGT GGCAGGGTTC GCGTGA
```

Exons/Introns (in Base Pairs) of SEQ ID NO: 1:

| Exons/Introns (in base pairs) of SEQ ID NO: 1: | |
|---|---|
| Exon 1 | 1-204 bp |
| Intron 1 | 205-254 bp |
| Exon 2 | 255-345 bp |
| Intron 2 | 346-399 bp |
| Exon 3 | 400-526 bp |
| Intron 3 | 527-580 bp |
| Exon 4 | 581-582 bp |
| Intron 4 | 583-644 bp |
| Exon 5 | 645-665 bp |
| Intron 5 | 666-716 bp |
| Exon 6 | 717-1168 bp |
| Intron 6 | 1169-1231 bp |
| Exon 7 | 1232-1288 bp |
| Intron 7 | 1289-1345 bp |
| Exon 8 | 1346-1396 bp |

Features (in Base Pairs) of SEQ ID NO: 1:

| Features (in base pairs) of SEQ ID NO: 1: | |
|---|---|
| Signal Peptide | 1-57 bp |
| Xylanase | 58-204, 255-345, 400-526, 581-582, 645-665, |
| Catalytic site | 717-1168, 1232-1288, 1346-1393 bp |
| Stop codon | 1394-1396 bp |

Protein Sequence of *Hohenbuehelia mastrucata* Strain NN009379 Protein (SEQ ID NO: 2):

```
  1  MKSALLVLTV TVPFAAAQAG LNRVAKAAGK LYFGTATNLE QFTDAPYFAV LNNVTEFGQI

61  TAANSMKWDA TEPSRGVFTF AQGDQIAALA QQNGQLLRGH NCVWHQQLPA WVTDGNFDAP

121  TLTSIVETHC STIVDHYKGQ IYSWDVINEC LNDDGTFRED VFFDTLNTSY IATALRAARA

181  ADPNAKLYIN DFNIEGTGPK STAMVNLVKS LQAQNVPIDG IGIQTHLIVG EVPSTLLENM

241  QQFTALGVEI AITELDIRMT LPDTPELRAQ QQQDYQTVIE ACNTVPECVG VTVWDFTDKY

301  SWVPGTFTGQ GDACPWDENI VRKSAYDGIV AGFA
```

| Features of SEQ ID NO: 2 (amino acid positions): | |
|---|---|
| Signal Peptide | 1-19 |
| Xylanase | 20-334 |
| Catalytic site | |

Signal Peptide Sequence of SEQ ID NO: 2:

MKSALLVLTVTVPFAAAQA

*Hohenbuehelia Mastrucata* Strain NN009379 Genomic Nucleotide Sequence (SEQ ID NO: 3):

```
   1  ATGAAGCTCG TGCCTGTCCT CATTGCAATT TCTGCAACCT TGGCTGCTGC TCAGGCGGGG TTAAATAAAG TGGCCAAGGC

81  CGCCGGGAAG AAATATTTCG GGACCGCGAC TAATAATAAC GAGTTCACAG ACGTTCCTA TTTCCCTGTA CTGAATAACG

161  TCACTGATTT TGGGCAGATT ACCGCAGCAA TTAGCATGAA ATGGGTATAT CCATCCATTA TCCTGTTTCT GGGAGACAAC

241  CTTGCTCACT TCCGAGTCGT TCTTAGGACG CAACGGAGCC ATCTCGTGGT ACATTTACGT TGCGCAGGG GAATGAAATT

321  GCCGCACTTG CCATAAAGAA CGGCCAGTTA CTTCGAGGTT GTGTCGTATC TGCTCAATCA CGTTTTAGTT GATTCATTTC

401  CTGCCCGCAG GCCATAACTG TGTATGGCAT CAGCAACTCC CTTCGTGGGT CACCAGTGGG AACTTCGATG TACCAACACT

481  ACCAAGCATC GTCTCGAGCC ACTGTCTACC CTIGTGGGAC GCTATAGAGG GCCTAGTGTG AGTGCTCCGG CTATGCCAGC

561  AGTCACGATT GTACTGATCT CCATTGATTT ACAGCTGTAT GTGTAGCATT GCATTGACAA TGGATATGGT TTCTTATTCA

641  CACTTTCGTC GCTAGATAGC TGGGATGTCA TCAATGGTGC GCGGGCTGTT GATTACAGTC GATGCCTATC TTCAACTGCG

721  CTACAGAATG CTTGAGAGAT GACGGAACCT TCCGCTCAGA TGTTTTCTCC AGGACCCTCG GGACCTCATA CATCGCCACT

801  GCCTTGCGTG CAGCGCGTGC CGCCGACCCA ACCGCCAAGC TTTACATCAG TGACTTCAAC ATCGAAGGCA CCGGAGCCAA

881  GTCCACCGCC ATGGTGAATC TCGTTAAATT CCTCCAATCG CAGGGCGTGC CTATCGACGG CATCGGGATC CAGGCGCATC

961  TCATTGTCGG TAAAGTCCGG AGCACACTAG TCGCGAATAT GCGCCAGTTC ACGGCATTGG GTGTGGAAAT TGCCTTTACC

1041  GAGCTGGACA TTCGAATGGC GCTCTCTGCG ACGCCGGCAT TACTCGCACA GCAGCAAAAG GATTACCAGA CTGTCATTGC

1121  TGCATGCAAG ACTGTGTCAG GCTGCGTGGG CGTCACCCTT TGGGATTTCA CGGACAAAGT TCGTCGCATG ACAGTCAATA

1201  TTTCGGACTT CATCAATCTG ATTCCTGCTT AACGAAGTAT TCTTGAGCCC CGGGAACGTT CGCAGGGCAG GGGGAAGCTT

1281  GCCCCTGGAT CAGCTGCGTG AATAGCGCAG GAATACTGTT CCATCCAACT GATGTCGTAT GTGATTTACA GAATATTGCC

1361  CGGAAGTTAG CCTATAACGG TATCATTTCT GGCTTCGCAT GA
```

Exons/Introns (in Base Pairs) of SEQ ID NO: 3:

| Exons/Introns (in base pairs) of SEQ ID NO: 3: | |
|---|---|
| Exon 1 | 1-204 bp |
| Intron 1 | 205-266 bp |
| Exon 2 | 267-357 bp |
| Intron 2 | 358-410 bp |
| Exon 3 | 411-537 bp |
| Intron 3 | 538-594 bp |
| Exon 4 | 595-602 bp |
| Intron 4 | 603-655 bp |
| Exon 5 | 656-676 bp |
| Intron 5 | 677-726 bp |
| Exon 6 | 727-1182 bp |
| Intron 6 | 1183-1247 bp |
| Exon 7 | 1248-1297 bp |
| Intron 7 | 1298-1351 bp |
| Exon 8 | 1352-1402 bp |

Features (in Base Pairs) of SEQ ID NO: 3:

| Features (in base pairs) of SEQ ID NO: 3: | |
|---|---|
| Signal Peptide | 1-57 bp |
| Xylanase | 58-204, 267-357, 411-537, 595-602, 656-676, 727-1182, 1248-1297, 1352-1399 bp |
| Catalytic site | |
| Stop codon | 1400-1402 bp |

Protein Sequence of *Hohenbuehelia mastrucata* Strain NN009379 Protein (SEQ ID NO: 4):

```
  1  MKLVPVLIAI SATLAAAQAG LNKVAKAAGK KYFGTATNNN EFTDASYFPV LNNVTDFGQI
 61  TAAISMKWDA TEPSRGTFTF AQGNEIAALA IKNGQLLRGH NCVWHQQLPS WVTSGNFDVP
121  TLPSIVSSHC LPLWDAIEGL VCMYSWDVIN ECLRDDGTFR SDVFSRTLGT SYIATALRAA
181  RAADPTAKLY ISDFNIEGTG AKSTAMVNLV KFLQSQGVPI DGIGIQAHLI VGKVRSTLVA
241  NMRQFTALGV EIAFTELDIR MALSATPALL AQQQKDYQTV IAACKTVSGC VGVTLWDFTD
301  KVPPGTFAGQ GEACPWISCN IARKLAYNGI ISGFA
```

Features of SEQ ID NO: 4 (Amino Acid Positions):

| Features of SEQ ID NO: 4 (amino acid positions): | |
|---|---|
| Signal Peptide | 1-19 |
| Xylanase | 20-335 |
| Catalytic site | |

Signal Peptide Sequence of SEQ ID NO: 4:

```
MKLVPVLIAISATLAAAQA
```

*Hohenbuehelia Mastrucata* Strain NN009379 Genomic Nucleotide Sequence (SEQ ID NO: 5):

```
  1  ATGACGGTCA AGGCTACTCT CGCCTTCAGC GCGCTGCTCT CTCTTCTACC TTTCGCCGTC GCACAGTCCG GCCCTTGGGG
 81  GCAATGTTCG TCGCCCATTT TGTACCAGTT TTTATACGCA ATACTGAGCT GTTCTTAGGT GGTGGAACGG GTTGGACTGG
161  TGCTACTACC TGCGTTGCTG GTTGGACTTG CATGTATAGC AATCCGTGGT ACTCCCAGTG TCTTCAAGGC GCGGTGAGCG
241  CATCCCTCCT TTTTTAAGCT GAGCCTACTC GTATCGCCAC ACGATGTTTC TGACAAACTT TCGTTATTGA ACGCCAGGCT
321  TCCAGCACGT CCGGAACGCC CAGCTCCAGC TCCAGCTCGT CTAGTTCTAG CACAGTTTCC AGCTCTACTG CTCTACCAAC
401  CGCCACATCC TCAGCTGGCC TTCATACAGT TGCCAAAGCC AAGGGCAAAC TCTACTTTGG TTCGGCAACC GATAACCCCG
481  AGCTTTCTGA CGCGACCTAC AAGGCTGGAC TTAGCAACAC CATGGAGTTT GGCCAGATTA CGCCTGGGAA CAGCATGAAA
561  TGGGTGCGTA TTGCATGGGT CTGTTGTGGT TACTCAAGCG CGAGACCTGA AGGATAACTA GGACGCAACC GAGCCCAGCC
641  GCGGAACATT CACGTTCACG AACGGTGACG TTATTGCCAA CCTGGCGGCT GCAAACGGCC AGCTTCTGCG AGGCGCGCAT
721  TTACGATTTC TTAATCTCGT AGTGATGTAT TCAAAAGCAT TCTAGGCCAC AATTGTGTCT GGCACAGTCA ACTCCCTAGC
801  TGGGTGACCG CCCGGTAACT TCAACGCCAC CGAGCTCACGA GCATCGTCCA GACTCACTGC AGCACTGTCG TCGGCCATTA
881  CAAGGGCAAA GCGTGAGTTT TCTCATTGTA TCACATCGTT TCTTTGACTA ACGAGTCATT TGCAGTTGTA AGTACTAAGC
```

-continued

```
 961 TCCTGGATAC ACAAACAAGA TAAACCACTT ATGTTTAAAT CTCCTTCAGA TTCATGGGAC GTTGTGAACG GTAAGATTTG
1041 TAAACTCATT GGCAGCATTC TTTATTTAAT GACGATCAAA TTATAGAGCC CTTCAATGAC GACGGCACAT TCCGCACCTC
1121 CGTCTTCTAC ACCACGCTCG GCACAGACTA CATTGCCACC GCGCTCAAGG CCGCGCGCGC CGCGGACCCG GACACAAAGC
1201 TGTACATCAA CGACTACAAC ATCGACGGCA CCGGCGCCAA GTCGACCGCG ATGGTCAACC TCGTGACACA GCTCAAGGCA
1281 GCTGGTGTGC CCATTGACGG TATCGGCATC CAAGGGCATC TCATCGTCGG CGCCGTGCCT TCGACTATCC AGGCCAACAT
1361 CGAGCAGTTC GCGGCACTCG GCGTCGAGGT CGCCATCACC GAGCTCGACA TCCGCATGAC ACTCCCAGTG ACGCCCGAGA
1441 AGCTCGCGCA GCAGAAAACG GACTACCAGA ACGTGATCAA GGCGTGCAAT GCCGTCCCCA AGTGCATCGG CGTTACGATT
1521 TGGGATTACA CTGATAAGGT GCGGTGCTGA ATCTTTTCGC TTCTTCGGCG ACGTGCGGCC TGACCTTTTG TGTACCCGAT
1601 AGTACTCGTG GATTCCCAGC GTGTTCAGCG GACAGGGCGC TGCGCTCCCT TGGGACGAGG TGTGTTCTCC GTTAATCGAT
1681 CTTTACTTTC CTGATTTTGA CCCGAATCTC CCAGAACTAC GTCAAGAAGC CCGCTTATGA CGGTATTGTC ACCGGCTTCG
1761 GCGTATGA
```

Protein Sequence of *Hohenbuehelia mastrucata* Strain NN009379 Protein (SEQ ID NO: 6):

```
  1 MTVKATLAFS ALLSLLPFAV AQSGPWGQCG GTGWTGATTC VAGWTCMYSN PWYSQCLQGA
 61 ASSTSGTPSS SSSSSSSSTV SSSTALPTAT SSAGLHTVAK AKGKLYFGSA TDNPELSDAT
121 YKAGLSNTME FGQITPGNSM KWDATEPSRG TFTFTNGDVI ANLAAANGQL LRGAHLRFLN
181 LVVIWVTAGN FNATELTSIV QTHCSTVVGH YKGKAYSWDV VNEPFNDDGT FRTSVFYTTL
241 GTDYIATALK AARAADPDTK LYINDYNIDG TGAKSTAMVN LVTQLKAAGV PIDGIGIQGH
301 LIVGAVPSTI QANIEQFAAL GVEVAITELD IRMTLPVTPE KLAQQKTDYQ NVIKACNAVP
361 KCIGVTIWDY TDKYSWIPSV FSGQGAALPW DENYVKKPAY DGIVTGFGV
```

Exons/Introns (in Base Pairs) of SEQ ID NO: 5:

| Exons/Introns (in base pairs) of SEQ ID NO: 5: | |
|---|---|
| Exon 1 | 1-85 bp |
| Intron 1 | 86-138 bp |
| Exon 2 | 139-233 bp |
| Intron 2 | 234-317 bp |
| Exon 3 | 318-563 bp |
| Intron 3 | 564-621 bp |
| Exon 4 | 622-746 bp |
| Intron 4 | 747-799 bp |
| Exon 5 | 800-892 bp |
| Intron 5 | 893-945 bp |
| Exon 6 | 946-947 bp |
| Intron 6 | 948-1009 bp |
| Exon 7 | 1010-1030 bp |
| Intron 7 | 1031-1086 bp |
| Exon 8 | 1087-1538 bp |
| Intron 8 | 1539-1602 bp |
| Exon 9 | 1603-1659 bp |
| Intron 9 | 1660-1714 bp |
| Exon 10 | 1715-1768 bp |

Features (in Base Pairs) of SEQ ID NO: 5:

| Features (in base pairs) of SEQ ID NO: 5: | |
|---|---|
| Signal Peptide | 1-63 bp |
| Cellulose Binding Module 1 (CBM 1) | 64-85, 139-227 bp |
| Linker | 228-233, 318-419 bp |
| Xylanase | 420-563, 622-746, 800-892, 946-947, |
| Catalytic site | 1010-1030,1087-1538, 1603-1659, 1715-1765 bp |
| Stop codon | 1766-1768 bp |

Features of SEQ ID NO: 6 (Amino Acid Positions):

| Features of SEQ ID NO: 6 (amino acid positions): | |
|---|---|
| Signal Peptide | 1-21 |
| Cellulose Binding Module 1 (CBM 1) | 22-59 |
| Linker | 59-94 |
| Xylanase | 95-409 |
| Catalytic site | |

Signal Peptide Sequence of SEQ ID NO: 6:

MTVKATLAFSALLSLLPFAVA

*Hohenbuehelia Mastrucata* Strain NN009379 Genomic
Nucleotide Sequence (SEQ ID NO: 7):

```
   1  ATGATGGTCA AGTTGTCTCT TACTGTCTTA GTCGCTGTCG TCGCTGGTCG TGTTTCGGCC GTCCCTGTTT GGGGCCAATG
  81  TCAGTGAGAT CATCGATCAT CGCTGATGTA TAGCTCGGAC TATTAACCGT GCACCTTATT GTAGGCGGTG GTCTGAATTG
 161  GACTGGCGGC GTACGTTCAT TTTCAATAAG TATTGCCCAC GTTAGCTGAC TTGTTACTTC TTCAGACAAC ATGTACGTCA
 241  AATTGTATGA AGTTCAGTAA GTAGATCCGT TGACCAGACT TACATTCAGG CGATACCGGA TCCACCTGTG TTAAGCAGAA
 321  CGACTGGTAC TCTCAGTTAG TCCTGCGATG CGTTCTCGCT CTATATAATT CCTAAACGAG ATGTTATACA GATGCTTGCC
 401  TGGTACACAA CCACAGCCGA CACCCACTCC GACGACTCCA ACATCGACGG TTGGCCCAAC GACCACTCCC ACTCCCACTA
 481  GCGGCTCCGG CTCCGGCCTC GATACTCACT TCAAGGCTAA GGGAAAGAAA TTCTGGGGCT CTTGCGCTGA TCCAGGCACA
 561  TTGAACATCG CCGGTATGTT GCTCGCATGA TGCGGGACTC CTAAAAGTTT ATCGTTGATC TGGGATTGAT CTGGGATTAT
 641  CCTATAGCAA ATGCCAATGT CCTGAAGGCA GAGTTCGGTC AGGTAACGCC GGAGAACTCT ATGAAGGTAC GAATTCCAAT
 721  CCCAACATCT CAAGATTGGG CTCAAATATA CCCTTATACT TAGTGGGACG CTACCGAACG TGTGTTATCA CTACATTTCA
 801  TTCGCTGAAC TGACATCTTG ACGAGGGTCA CGACTCACAG CCAGCCGCAA CCAATTCAAC TTTGGCAATG CTGATACGCT
 881  CGTCAACTGG GCTATCTCAA ACGGCAAACT GATCCGCGGT CACACTTGG GTACAGTCAA TATTTTCTCT TACCGTGCTC
 961  TCTCATTGAC GGTATCCTCT AGTCTGGCAT TCACAGCTGC CGGGCTGGGT TTCGGCCATC AACGATAAGA CCACTTGGT
1041  TTGTCACTTT GTATTTTCAC GCGTAGCGGC ATTTTGATTG ATTGCATCGA TTACAGACCT CCGTCATCCA AAACCACATC
1121  TCCAATCTTG CTGGAAGATA CGCAGGCAAA CTTTACGGTT AGTCATGTCT GTTTCCTTGA ACATTAACGG ACACTCATGT
1201  AAGTGATTTT TGGCATCTAG CTGTAAGCAT TCACCCAAAC GTACGCTCTT CTGGTCCTGA CGCTTTTCAC TTCCACAGTG
1281  GGACGTCGTC AAGTAAGTCG CTCCCCTTCG ACCATGCGAA TCCACGGCCT ATGATACTCT TTTAGTGAAA TATTCAACGA
1361  GGATGGCTCC CTTCGCTCCA GTGTCTTCTC CAACGTCCTC GGCGAGGTAC TCTACCCCGT CAATAGATCT ATTTTCCACG
1441  CTTTTACTGA CAATGGAAAA CCTGAATGTA GTCCTTCGTC ACTATCGCCT TCCAAGCTGC AAAGGCCGCC GATCCTAGCG
1521  CCAAGTTAGT GAAACTCTCA GTACGATAAG TAGAGATCAG CGCCGATGAT TTATGTACTT ACAGGCGCTA CATCAATGAC
1601  TACAATCTAG ACTCAAACAA TGCAAAGTT CAAGGTTAGC CATTTACACT GTGCGCCGAG CCGATGCCCG GGGGTCTAAC
1681  TTCTGGCTGC AGGTCTGGTT GCCCTTGTGA AGCGCGTCAA CAGCGCCAAC GCGGACCTCA TCCAGGGCAT TGGCACGCAG
1761  ATGCACCTTA GTGTACGTGT CCCCCTTCTT GCGCCCACGA CGGAACTTCT GAATCCACGC ACTTCATAAT AGGCCGGCGG
1841  TGTTGGCGGT GTCCAAGCTG CCCTGACCGC CCTCGCTGGT GCTGGTGTGT CCGAAGTCGC AATCACCGAG CTCGACATCG
1921  TCAACGCTGC GCCAAACGAC TACGTCACCG TTGCCAAGGC CTGCCTCAAT ACGCCCGCTT GCGTGGCGAT TACGAGCTGG
2001  GGTGTTTCCG ACCAGGTGCG TTGTGCGGTT TTCCTGGTTT CATTTGCACT ACATCTAACA CGCGTTCTAC GAATAGAACT
2081  CCTGGCGAGC CAGTTCTACC CCTCTCCTGT TTAACAACAA CTACCAGCCT AAGCCGGCAT ACACAGCAGT CATCCAGGCG
2161  CTCGCCTGA
```

Exons/Introns (in Base Pairs) of SEQ ID NO: 7:

| Exons/Introns (in base pairs) of SEQ ID NO: 7: | |
|---|---|
| Exon 1 | 1-79 bp |
| Intron 1 | 80-144 bp |
| Exon 2 | 145-170 bp |
| Intron 2 | 171-225 bp |
| Exon 3 | 226-232 bp |
| Intron 3 | 233-289 bp |
| Exon 4 | 290-335 bp |
| Intron 4 | 336-391 bp |
| Exon 5 | 392-573 bp |
| Intron 5 | 574-647 bp |
| Exon 6 | 648-706 bp |
| Intron 6 | 707-763 bp |
| Exon 7 | 764-779 bp |
| Intron 7 | 780-840 bp |
| Exon 8 | 841-930 bp |
| Intron 8 | 931-982 bp |
| Exon 9 | 983-1038 bp |
| Intron 9 | 1039-1096 bp |
| Exon 10 | 1097-1157 bp |
| Intron 10 | 1158-1220 bp |
| Exon 11 | 1221-1240 bp |
| Intron 11 | 1241-1278 bp |
| Exon 12 | 1279-1292 bp |
| Intron 12 | 1293-1345 bp |
| Exon 13 | 1346-1406 bp |
| Intron 13 | 1407-1471 bp |
| Exon 14 | 1472-1524 bp |
| Intron 14 | 1525-1584 bp |
| Exon 15 | 1585-1634 bp |
| Intron 15 | 1635-1692 bp |

Exons/Introns (in base pairs) of SEQ ID NO: 7:

| | |
|---|---|
| Exon 16 | 1693-1772 bp |
| Intron 16 | 1773-1832 bp |
| Exon 17 | 1833-2015 bp |
| Intron 17 | 2016-2076 bp |
| Exon 18 | 2077-2166 bp |

Features (in Base Pairs) of SEQ ID NO: 7:

Features (in base pairs) of SEQ ID NO: 7:

| | |
|---|---|
| Signal Peptide | 1-60 bp |
| Cellulose Binding Module 1 (CBM 1) | 61-79, 145-170, 226-232, 290-335, 392-401 bp |

Features (in base pairs) of SEQ ID NO: 7:

| | |
|---|---|
| Linker | 402-497 bp |
| Xylanase | 498-573, 648-706, 764-779, 841-930, 983-1038, |
| Catalytic site | 1097-1157, 1221-1240, 1279-1292, 1346-1406, |
| | 1472-1524, 1585-1634, 1693-1772, 1833-2015, |
| | 2077-2166 bp |
| Stop codon | 2167-2169 bp |

Protein Sequence of *Hohenbuehelia mastrucata* Strain NN009379 Protein (SEQ ID NO: 8):

```
  1  MMVKLSLTVL VAVVAGRVSA VPVWGQCGGL NWTGGTTCDT GSTCVKQNDW YSQCLPGTQP
 61  QPTPTPTTPT STVGPTTTPT PTSGSGSGLD THFKAKGKKF WGSCADPGTL NIAANANVLK
121  AEFGQVTPEN SMKWDATEPS RNQFNFGNAD TLVNWAISNG KLIRGHTLVW HSQLPGWVSA
181  INDKTTLTSV IQNHISNLAG RYAGKLYAVS IHPNWDVVNE IFNEDGSLRS SVFSNVLGES
241  FVTIAFQAAK AADPSAKRYI NDYNLDSNNA KVQGLVALVK RVNSANADLI QGIGTQMHLS
301  AGGVGGVQAA LTALAGAGVS EVAITELDIV NAAPNDYVTV AKACLNTPAC VAITSWGVSD
361  QNSWRASSTP LLFNNNYQPK PAYTAVIQAL A
```

Features of SEQ ID NO: 8 (Amino Acid Positions):

| Features of SEQ ID NO: 8 (amino acid positions): | |
|---|---|
| Signal Peptide | 1-20 |
| Cellulose Binding Module 1 (CBM 1) | 21-56 |
| Linker | 57-88 |
| Xylanase Catalytic site | 89-391 |

Signal Peptide Sequence of SEQ ID NO: 8:

MMVKLSLTVLVAVVAGRVSA

*Hohenbuehelia Mastrucata* Strain NN009379 Genomic Nucleotide Sequence (SEQ ID NO: 9):

```
  1  ATGTTTAAAT TGCTTTCTGT GGTCTCTCTT GCCATTGTTG CAGGCCGTGT CAGCGCTGTC CCCGTCTGGG GTCAATGTGA
 81  GTATGCTACT TCTTCTGTCC TGTGATCAAA ACCTGATATC CGAGTTGTTA GGTGGTGGCA TCGGTTGGAC CGGCGGAGTA
161  GGTGCCTTTC ACGACGTTTT GTGATGGCTC TCTGACCACA GCTGATTTAC TCGATGATTT CAGACTACAT GTAAGTTTTG
241  CCTATCATTT GACTCTATTC GCCATCAATT GAAGAGTCAT TATGATCCAG GTGATGCTGG AACCACCTGC ATCAAATTGA
321  ATGACTACTA TTCTCAGTGA GTTTCCCTAA AATATTTAAC AAAATCCCTC TCAATTGTTG CAGGTGCCAG CCCGGTGCAT
401  CGGCGCCCCC TCCAACCTCG GTGCCGCCCC CGCCGCCGAC AACCAGTGTG CCTTCCGGTC CTACTCCTAC TGGTGGACTC
481  AACAGCCATT TCGTCGCACA CGGAAAGAAG TTCTGGGGCT CCTGCGCTGA CTCTAATACC CTCAATATTG CTGGTAAATT
561  ACACTGAAGG CCTTTGGCTC AGGTTTAAAG TGTTGAAGGT TTTTATATTT CACAGCCAAC GCCGCCGTGT TGAAGTCTGA
641  CTTCGGTGCT GTCACTCCTG AAAACTCGAT GAAGGTACGT TTTCAGCATG GCTGTACTCA AAACCTTACT CACACGTTTA
721  TCTCAGTGGG ATGCAACTGA ACGTACGTAA ATTGTGGCTT GGATTCACTC TTCCAGGTTT ATTGAGCCGC GCTGCATTTG
801  TCAGCCTCGC GAGGTCAGTT CTCGTACTCC GGCGCTGACG CACTCGTCAA CTGGGCCGTG TCCAACGGCA AGCTGATCCG
```

```
 881  AGGACACACT CTTGGTCAGT TTCCATTGTT TTCGCGCCTC GTCCTCGGAT CCTTATCGAA TGCCTTGCAT AGTATGGCAC
 961  TCCCAGCTCC CGTCATGGGT ATCGGCGATT AACGACAAGA CCACCTTGGT AGGTTCTACC ATTGGTCCAT AATTCCGTCT
1041  GCTCAACCTT GTATAGACGT CCGTCATCCA AAACCACATC TCGAACCTTG CTGGCAGATA CAACGGAAAA CTCTATGGTG
1121  AGCGCTGTTA GTTAGTTGAT GTCTACATTT AGCTGACTTA ATACACGCAG CTGTAAGTCG GATGCGTTTA ATTTCGCCGT
1201  TGTTTTAACA ATGCTCTTTG ATTTTCCTCC TAGTGGGACG TTTGCAAGTG AGTCAACGTG AAGTTGTCCT TTCTTTTTCA
1281  AAACAACTGA GCATCACCCT GTGTCTAGCG AAATCTTCAA CGAAGATGGT ACCCTCCGCT CCAGCGTCTT CTCCAATGTT
1361  CTTGGCGAGG TACACTTGCT ATGGCTACTT TCTAATTTAG CTTACCCAT CCTTTCCTTG CGCAGTCTTT CGTCACTATT
1441  GCATTCCAAG CTGCGCGCGC TGCAGACTCC ACCGCCAAGT TCGATTGTTC TTTGATACCA AGGTTTGACC TATTCTTATT
1521  TGGCTCACTA CAGGCTCTAC ATCAACGACT ACAACCTCGA CTCGAACAAC GCCAAGGTTC AGGGTACGTT GACAGAAATC
1601  GGAATCCATC GAGGCCCATC ATTAATTATT CTGATCGCCC TCAGGCATGG TCGCCCTCGT CAAGCGCGTG AATGCCAACG
1681  GCAAACTCAT CGACGGTATT GGTACACAGA TGCACTTGAG TGTGCGTCCC GCTTCTATGA ACTAAAGATC TTCTCCATGT
1761  TAACATATTC TTTCCCCTAG GCCGGTGGTG CTGGIGGTGC CAAGCTGCC CTGACCGCGC TCGCTAGCTC CGGTGTGGGT
1841  GAGATCGCGA TCACAGAGCT CGACATTGTC AACGCATCGC CCAATGACTA TACCACTGTC GTCAATGCTT GCCTTAACAC
1921  GCCTGCTTGC ATTTCAATCA CCAGCTGGGG TGTCTCCGAT ACGGTGCGTG TTCACAGTCC TGCATGATTT CGTCTTTCCG
2001  ATCATGTCTG TCACTGCGTC CTTTCATCGC GGTATTATAG AACTCGTGGC GCGCAAGCTC TACCCCGCTC TTGTTCGACG
2081  GCAACTACAA GCCCAAACCA GCGTACACCG CGATCATGCA ACTTCTCGGA TGA
```

Exons/Introns (in Base Pairs) of SEQ ID NO: 9:

| Exons/Introns (in base pairs) of SEQ ID NO: 9: | |
|---|---|
| Exon 1 | 1-76 bp |
| Intron 1 | 77-131 bp |
| Exon 2 | 132-157 bp |
| Intron 2 | 158-223 bp |
| Exon 3 | 224-230 bp |
| Intron 3 | 231-290 bp |
| Exon 4 | 291-336 bp |
| Intron 4 | 337-383 bp |
| Exon 5 | 384-553 bp |
| Intron 5 | 554-615 bp |
| Exon 6 | 616-674 bp |
| Intron 6 | 675-726 bp |
| Exon 7 | 727-742 bp |
| Intron 7 | 743-804 bp |
| Exon 8 | 805-894 bp |
| Intron 8 | 895-952 bp |
| Exon 9 | 953-1008 bp |
| Intron 9 | 1009-1056 bp |
| Exon 10 | 1057-1117 bp |
| Intron 10 | 1118-1152 bp |
| Exon 11 | 1153-1172 bp |
| Intron 11 | 1173-1233 bp |
| Exon 12 | 1234-1247 bp |
| Intron 12 | 1248-1308 bp |
| Exon 13 | 1309-1369 bp |
| Intron 13 | 1370-1425 bp |
| Exon 14 | 1426-1478 bp |
| Intron 14 | 1479-1533 bp |
| Exon 15 | 1534-1583 bp |
| Intron 15 | 1584-1644 bp |
| Exon 16 | 1645-1721 bp |
| Intron 16 | 1722-1780 bp |
| Exon 17 | 1781-1963 bp |
| Intron 17 | 1964-2040 bp |
| Exon 18 | 2041-2130 bp |

Features (in Base Pairs) of SEQ ID NO: 9:

| Features (in base pairs) of SEQ ID NO: 9: | |
|---|---|
| Signal Peptide | 1-57 bp |
| Cellulose Binding Module 1 (CBM 1) | 58-76, 132-157, 224-230, 291-336, 384-393 bp |
| Linker | 394-477 bp |
| Xylanase | 478-553, 616-674, 727-742, 805-894, 953-1008, 1057-1117, 1153-1172, 1234-1247, 1309-1369, 1426-1478, 1534-1583, 1645-1721, 1781-1963, 2041-2130 bp |
| Catalytic site | |
| Stop codon | 2131-2133 bp |

Protein Sequence of *Hohenbuehelia mastrucata* Strain NN009379 Protein (SEQ ID NO: 10):

```
  1  MFKLLSVVSL AIVAGRVSAV PVWGQCGGIG WTGGTTCDAG TTCIKLNDYY SQCQPGASAP
 61  PPTSVPPPPP TTSVPSGPTP TGGLNSHFVA HGKKFWGSCA DSNTLNIAAN AAVLKSDFGA
121  VTPENSMKWD ATEPSRGQFS YSGADALVNW AVSNGKLIRG HTLVWHSQLP SWVSAINDKT
181  TLTSVIQNHI SNLAGRYNGK LYADLIHAAW DVCNEIFNED GTLRSSVFSN VLGESFVTIA
241  FQAARAADST AKLYINDYNL DSNNAKVQGM VALVKRVNAN GKLIDGIGTQ MHLSAGGAGG
```

```
-continued
301 AQAALTALAS SGVGEIAITE LDIVNASPND YTTVVNACLN TPACISITSW GVSDTNSWRA

361 SSTPLLFDGN YKPKPAYTAI MQLLG
```

Features of SEQ ID NO: 10 (Amino Acid Positions):

| Features of SEQ ID NO: 10 (amino acid positions): | |
|---|---|
| Signal Peptide | 1-19 |
| Cellulose Binding Module 1 (CBM 1) | 20-55 |
| Linker | 56-83 |
| Xylanase Catalytic site | 84-385 |

Signal Peptide Sequence of SEQ ID NO: 10:

MFKLLSVVSLAIVAGRVSA

DEFINITIONS

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer. In one aspect, the polypeptides of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO: 2, SEQ ID NO: 4, SEQ ID NO: 6, SEQ ID NO: 8, or SEQ ID NO: 10.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has xylanase activity. In one aspect, a fragment contains at least 20 amino acid residues, e.g., at least 30 to 333 amino acid residues or at least 50 to 330, 80 to 310, 100 to 290, 150 to 270, or 200 to 250, or any number in between, amino acid residues of SEQ ID NO: 2. In another aspect, a fragment contains at least 20 amino acid residues, e.g., at least 30 to 334 amino acid residues or at least 50 to 330, 80 to 310, 100 to 290, 150 to 270, or 200 to 250, or any number in between, amino acid residues of SEQ ID NO: 4. In another aspect, a fragment contains at least 20 amino acid residues, e.g., at least 30 to 408 amino acid residues or at least 50 to 400, 80 to 380, 100 to 350, 150 to 300, or 200 to 250, or any number in between, amino acid residues of SEQ ID NO: 6. In another aspect, a fragment contains at least 20 amino acid residues, e.g., at least 30 to 390 amino acid residues or at least 50 to 380, 80 to 350, 100 to 330, 150 to 300, or 200 to 250, or any number in between, amino acid residues of SEQ ID NO: 8. In another aspect, a fragment contains at least 20 amino acid residues, e.g., at least 30 to 384 amino acid residues or at least 50 to 380, 80 to 360, 100 to 340, 150 to 300, or 200 to 250, or any number in between, amino acid residues of SEQ ID NO: 10.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 334 of SEQ ID NO: 2 based on the SignalP program (Nielsen et al., 1997, Protein Engineering 10:1-6) that predicts amino acids 1 to 19 of SEQ ID NO: 2 are a signal peptide. In another aspect, the mature polypeptide is amino acids 1 to 334 of SEQ ID NO: 2. In another aspect, the mature polypeptide is amino acids 20 to 335 of SEQ ID NO: 4 based on the SignalP program that predicts amino acids 1 to 19 of SEQ ID NO: 4 are a signal peptide. In another aspect, the mature polypeptide is amino acids 1 to 335 of SEQ ID NO: 4. In another aspect, the mature polypeptide is amino acids 22 to 409 of SEQ ID NO: 6 based on the SignalP program that predicts amino acids 1 to 21 of SEQ ID NO: 6 are a signal peptide. In another aspect, the mature polypeptide is amino acids 1 to 409 of SEQ ID NO: 6. In another aspect, the mature polypeptide is amino acids 21 to 391 of SEQ ID NO: 8 based on the SignalP program that predicts amino acids 1 to 20 of SEQ ID NO: 8 are a signal peptide. In another aspect, the mature polypeptide is amino acids 1 to 391 of SEQ ID NO: 8. In another aspect, the mature polypeptide is amino acids 20 to 385 of SEQ ID NO: 10 based on the SignalP program that predicts amino acids 1 to 19 of SEQ ID NO: 10 are a signal peptide. In another aspect, the mature polypeptide is amino acids 1 to 385 of SEQ ID NO: 10. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 58 to 1393 of SEQ ID NO: 1 or the cDNA sequence thereof based on the SignalP program (Nielsen et al., 1997, supra) that predicts nucleotides 1 to 57 of SEQ ID NO: 1 encode a signal peptide. In another aspect, the mature polypeptide coding sequence is nucleotides 1 to 1393 of SEQ ID NO: 1 or the cDNA sequence thereof. In another aspect, the mature polypeptide coding sequence is nucleotides 58 to 1399 of SEQ ID NO: 3 or the cDNA sequence thereof based on the SignalP program that predicts nucleotides 1 to 57 of SEQ ID NO: 3 encode a signal peptide. In another aspect, the mature polypeptide coding sequence is nucleotides 1 to 1399 of SEQ ID NO: 3 or the cDNA sequence thereof. In another aspect, the mature polypeptide coding sequence is nucleotides 64 to 1765 of SEQ ID NO: 5 or the cDNA sequence thereof based on the SignalP program that predicts nucleotides 1 to 63 of SEQ ID NO: 5 encode a signal peptide. In another aspect, the mature polypeptide coding sequence is nucleotides 1 to 1765 of SEQ ID NO: 5 or the cDNA sequence thereof. In another aspect, the mature polypeptide coding sequence is nucleotides 61 to 2166 of SEQ ID NO: 7 or the cDNA sequence thereof based on the SignalP program that predicts nucleotides 1 to 60 of SEQ ID NO: 7 encode a signal peptide. In another aspect, the mature polypeptide coding sequence is nucleotides 1 to 2166 of SEQ ID NO: 7 or the cDNA sequence thereof. In another aspect, the mature polypeptide coding sequence is nucleotides 58 to 2130 of SEQ ID NO: 9 or the cDNA sequence thereof based on the SignalP program that predicts nucleotides 1 to 57 of SEQ ID NO: 9 encode a signal peptide. In another aspect, the mature polypeptide coding sequence is nucleotides 1 to 2130 of SEQ ID NO: 9 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 22 to 59 of SEQ ID NO: 6. In one embodiment the CBM is amino acids 21 to 56 of SEQ ID NO: 8. In one embodiment the CBM is amino acids 20 to 55 of SEQ ID NO: 10. The CBM is separated from the catalytic domain by a linker sequence. The linker is in one embodiment amino acids 59 to 94 of SEQ ID NO: 6. The linker is in one embodiment amino acids 57 to 88 of SEQ ID NO: 8. The linker is in one embodiment amino acids 56 to 83 of SEQ ID NO: 10.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity. In one aspect, a subsequence contains at least 800 nucleotides, e.g., at least 1000 nucleotides or at least 1100 nucleotides of SEQ ID NO: 1. In another aspect, a subsequence contains at least 800 nucleotides, e.g., at least 1000 nucleotides or at least 1100 nucleotides of SEQ ID NO: 3. In another aspect, a subsequence contains at least 1000 nucleotides, e.g., at least 1200 nucleotides or at least 1500 nucleotides of SEQ ID NO: 5. In another aspect, a subsequence contains at least 1000 nucleotides, e.g., at least 1200 nucleotides or at least 1500 nucleotides of SEQ ID NO: 7. In another aspect, a subsequence contains at least 1000 nucleotides, e.g., at least 1200 nucleotides or at least 1500 nucleotides of SEQ ID NO: 9.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

DETAILED DESCRIPTION OF THE INVENTION

Polypeptides Having Xylanase Activity

In an embodiment, the present invention relates to isolated polypeptides having a sequence identity to the mature polypeptide of SEQ ID NO: 2 of at least 68%, e.g., at least 69%, at least 70%, at least 75%, at least 80%, at least 85%, at least 87%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 4 of at least 64%, e.g., at least 65%, at least 67%, at least 70%, at least 75%, at least 80%, at least 85%, at least 87%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 6 of at least 70%, e.g., at least 71%, at least 72%, at least 73%, at least 75%, at least 80%, at least 85%, at least 87%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 8 of at least 74%, e.g., at least 75%, at least 76%, at least 77%, at least 80%, at least 85%, at least 87%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 10 of at least 75%, e.g., at least 76%, at least 77%, at least 80%, at least 85%, at least 87%, at least 90%, at least 91%, at least 92%, at least 93%, at least 94%, at least 95%, at least 96%, at least 97%, at least 98%, at least 99%, or 100%, which have xylanase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, SEQ ID NO: 8, or SEQ ID NO: 10.

A polypeptide of the present invention preferably comprises or consists of the amino acid sequence of SEQ ID NO: 2, SEQ ID NO: 4, SEQ ID NO: 6, SEQ ID NO: 8, or SEQ ID NO: 10 or an allelic variant thereof; or is a fragment thereof having xylanase activity. In another aspect, the polypeptide comprises or consists of the mature polypeptide of SEQ ID NO: 2, SEQ ID NO: 4, SEQ ID NO: 6, SEQ ID NO: 8, or SEQ ID NO: 10. In another aspect, the polypeptide comprises or consists of amino acids 20 to 334 of SEQ ID NO: 2, amino acids 20 to 335 of SEQ ID NO: 4, amino acids 22 to 409 of SEQ ID NO: 6, amino acids 21 to 391 of SEQ ID NO: 8, or amino acids 20 to 385 of SEQ ID NO: 10.

In another embodiment, the present invention relates to an isolated polypeptide having xylanase activity encoded by a polynucleotide that hybridizes under very low stringency conditions, or low stringency conditions, or medium stringency conditions, or medium-high stringency conditions, or high stringency conditions, or very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, or SEQ ID NO: 9, or a subsequence thereof, as well as the polypeptide of SEQ ID NO: 2, SEQ ID NO: 4, SEQ ID NO: 6, SEQ ID NO: 8, or SEQ ID NO: 10, or a fragment thereof, may be used to design nucleic acid probes to identify and clone DNA encoding polypeptides having xylanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^3$H, $^{35}$S, biotin, or avidin). Such probes are encompassed by the present invention.

A genomic DNA or cDNA library prepared from such other strains may be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, or SEQ ID NO: 9 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, or SEQ ID NO: 9; (ii) the mature polypeptide coding sequence of SEQ ID NO: 1, SEQ ID NO: 3, SEQ ID NO: 5, SEQ ID NO: 7, or SEQ ID NO: 9; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, or SEQ ID NO: 10; the mature polypeptide thereof; or a fragment thereof. In another aspect, the nucleic acid probe is SEQ ID NO: 1, SEQ ID NO: 3, SEQ ID NO: 5, SEQ ID NO: 7, or SEQ ID NO: 9; or the cDNA sequence thereof. In another aspect, the nucleic acid probe is the polynucleotide contained in *Hohenbuehelia mastrucata* Strain NN009379, wherein the polynucleotide encodes a polypeptide having xylanase activity.

In another embodiment, the present invention relates to an isolated polypeptide having xylanase activity encoded by a polynucleotide having a sequence identity to the mature polypeptide coding sequence of SEQ ID NO: 1, SEQ ID NO: 3, SEQ ID NO: 5, SEQ ID NO: 7, or SEQ ID NO: 9, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, or SEQ ID NO: 10 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, or SEQ ID NO: 10 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having [Enzyme] Activity

A polypeptide having xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Hohenbuehelia* polypeptide.

In another aspect, the polypeptide is a *Hohenbuehelia mastrucata* polypeptide, e.g., a polypeptide obtained from *Hohenbuehelia mastrucata* Strain NN009379.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 20 to 334 of SEQ ID NO: 2), a catalytic domain having at least 60% sequence identity to the catalytic domain of SEQ ID NO: 4 (for example, amino acids 20 to 335 of SEQ ID NO: 4), a catalytic domain having at least 60% sequence identity to the catalytic domain of SEQ ID NO: 6 (for example, amino acids 95 to 409 of SEQ ID NO: 6), a catalytic domain having at least 60% sequence identity to the catalytic domain of SEQ ID NO: 8 (for example, amino acids 89 to 391 of SEQ ID NO: 8), or a catalytic domain having at least 60% sequence identity to the catalytic domain of SEQ ID NO: 10 (for example, amino acids 84 to 385 of SEQ ID NO: 10);

(b) a catalytic domain encoded by a polynucleotide having at least 60% sequence identity to the catalytic domain coding sequence of SEQ ID NO: 1 (for example, nucleotides 58-204, 255-345, 400-526, 581-582, 645-665, 717-1168, 1232-1288, and 1346-1393 of SEQ ID NO: 1), a catalytic domain encoded by a polynucleotide having at least 60% sequence identity to the catalytic domain coding sequence of SEQ ID NO: 3 (for example, nucleotides 58-204, 267-357, 411-537, 595-602, 656-676, 727-1182, 1248-1297, and 1352-1399 of SEQ ID NO: 3), a catalytic domain encoded by a polynucleotide having at least 60% sequence identity to the catalytic domain coding sequence of SEQ ID NO: 5 (for example, nucleotides 420-563, 622-746, 800-892, 946-947, 1010-1030, 1087-1538, 1603-1659, and 1715-1765 of SEQ ID NO: 5), a catalytic domain encoded by a polynucleotide having at least 60% sequence identity to the catalytic domain coding sequence of SEQ ID NO: 7 (for example, nucleotides 498-573, 648-706, 764-779, 841-930, 983-1038, 1097-1157, 1221-1240, 1279-1292, 1346-1406, 1472-1524, 1585-1634, 1693-1772, 1833-2015, and 2077-2166 of SEQ ID NO: 7), or a catalytic domain encoded by a polynucleotide having at least 60% sequence identity to the catalytic domain coding sequence of SEQ ID NO: 9 (for example, nucleotides 478-553, 616-674, 727-742, 805-894, 953-1008, 1057-1117, 1153-1172, 1234-1247, 1309-1369, 1426-1478, 1534-1583, 1645-1721, 1781-1963, and 2041-2130 of SEQ ID NO: 9);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, or SEQ ID NO: 10; and (d) a fragment of a catalytic domain of (a), (b), or (c), which has xylanase activity.

The catalytic domain preferably has a degree of sequence identity to the catalytic domain of SEQ ID NO: 2, SEQ ID NO: 4, SEQ ID NO: 6, SEQ ID NO: 8, or SEQ ID NO: 10 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, SEQ ID NO: 6, SEQ ID NO: 8, or SEQ ID NO: 10.

The catalytic domain preferably comprises or consists of the catalytic domain of SEQ ID NO: 2 or an allelic variant thereof; or is a fragment thereof having xylanase activity. In another preferred aspect, the catalytic domain comprises or consists of amino acids 20 to 334 of SEQ ID NO: 2.

The catalytic domain preferably comprises or consists of the catalytic domain of SEQ ID NO: 4 or an allelic variant thereof; or is a fragment thereof having xylanase activity. In another preferred aspect, the catalytic domain comprises or consists of amino acids 20 to 335 of SEQ ID NO: 4.

The catalytic domain preferably comprises or consists of the catalytic domain of SEQ ID NO: 6 or an allelic variant thereof; or is a fragment thereof having xylanase activity. In another preferred aspect, the catalytic domain comprises or consists of amino acids 95 to 409 of SEQ ID NO: 6.

The catalytic domain preferably comprises or consists of the catalytic domain of SEQ ID NO: 8 or an allelic variant thereof; or is a fragment thereof having xylanase activity. In another preferred aspect, the catalytic domain comprises or consists of amino acids 89 to 391 of SEQ ID NO: 8.

The catalytic domain preferably comprises or consists of the catalytic domain of SEQ ID NO: 10 or an allelic variant thereof; or is a fragment thereof having xylanase activity. In another preferred aspect, the catalytic domain comprises or consists of amino acids 84 to 385 of SEQ ID NO: 10.

In an embodiment, the catalytic domain may be encoded by a polynucleotide that hybridizes under very low stringency conditions, or low stringency conditions, or medium stringency conditions, or medium-high stringency conditions, or high stringency conditions, or very high stringency conditions (as defined above) with (i) the catalytic domain coding sequence of SEQ ID NO: 1, SEQ ID NO: 3, SEQ ID NO: 5, SEQ ID NO: 7, or SEQ ID NO: 9, (ii) the cDNA sequence contained in the catalytic domain coding sequence of SEQ ID NO: 1, SEQ ID NO: 3, SEQ ID NO: 5, SEQ ID NO: 7, or SEQ ID NO: 9, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, SEQ ID NO: 5, SEQ ID NO: 7, or SEQ ID NO: 9 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having xylanase activity.

In one aspect, the polynucleotide encoding the catalytic domain comprises or consists of nucleotides 58 to 1393 of SEQ ID NO: 1 or the cDNA sequence thereof. In particular the polynucleotide encoding the catalytic domain comprises or consists of nucleotides 58-204, 255-345, 400-526, 581-582, 645-665, 717-1168, 1232-1288, and 1346-1393 of SEQ ID NO: 1.

In one aspect, the polynucleotide encoding the catalytic domain comprises or consists of nucleotides 58 to 1399 of SEQ ID NO: 3 or the cDNA sequence thereof. In particular the polynucleotide encoding the catalytic domain comprises or consists of nucleotides 58-204, 267-357, 411-537, 595-602, 656-676, 727-1182, 1248-1297, and 1352-1399 of SEQ ID NO: 3.

In one aspect, the polynucleotide encoding the catalytic domain comprises or consists of nucleotides 420 to 1765 of SEQ ID NO: 5 or the cDNA sequence thereof. In particular the polynucleotide encoding the catalytic domain comprises or consists of nucleotides 420-563, 622-746, 800-892, 946-947, 1010-1030, 1087-1538, 1603-1659, and 1715-1765 of SEQ ID NO: 5.

In one aspect, the polynucleotide encoding the catalytic domain comprises or consists of nucleotides 498 to 2166 of SEQ ID NO: 7 or the cDNA sequence thereof. In particular the polynucleotide encoding the catalytic domain comprises or consists of nucleotides 498-573, 648-706, 764-779, 841-930, 983-1038, 1097-1157, 1221-1240, 1279-1292, 1346-1406, 1472-1524, 1585-1634, 1693-1772, 1833-2015, and 2077-2166 of SEQ ID NO: 7.

In one aspect, the polynucleotide encoding the catalytic domain comprises or consists of nucleotides 478 to 2130 of SEQ ID NO: 9 or the cDNA sequence thereof. In particular the polynucleotide encoding the catalytic domain comprises or consists of nucleotides 478-553, 616-674, 727-742, 805- 894, 953-1008, 1057-1117, 1153-1172, 1234-1247, 1309-1369, 1426-1478, 1534-1583, 1645-1721, 1781-1963, and 2041-2130 of SEQ ID NO: 9.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Hohenbuehelia*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, or SEQ ID NO: 9, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, J. Bacteriol. 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlabia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlabia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a Hohenbuehelia cell. In a more preferred aspect, the cell is a Hohenbuehelia mastrucata cell. In a most preferred aspect, the cell is Hohenbuehelia mastrucata Strain NN009379.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having xylanase activity, or compositions thereof.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate.

DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, Microbiol. Mol. Biol. Reviews 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt %, e.g., 20-70 wt % or 30-60 wt %, such as around 40 wt %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having xylanase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the cellulase is preferably one or more (e.g., several) enzymes selected from the group consisting of an endoglucanase, a cellobiohydrolase, and a beta-glucosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having xylanase activity depend on several factors including, but not limited to, the mixture of component cellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having xylanase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having xylanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum,*

*Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material or xylan-containing material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof. The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material or xylan-containing material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 µM to about 10 mM, about 5 µM to about 5 mM, ord about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis.*

In a preferred aspect, the yeast is *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum.*

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 19 of SEQ ID NO: 2, amino acids 1 to 19 of SEQ ID NO: 4, amino acids 1 to 21 of SEQ ID NO: 6, amino acids 1 to 20 of SEQ ID NO: 8, or amino acids 1 to 19 of SEQ ID NO: 10. The polynucleotide may further comprise a gene encoding a protein, which is operably linked to the signal peptide. The protein is preferably foreign to the signal peptide. In one aspect, the polynucleotide encoding the signal peptide is nucleotides 1 to 57 of SEQ ID NO: 1. In another aspect, the polynucleotide encoding the signal peptide is nucleotides 1 to 57 of SEQ ID NO: 3. In another aspect, the polynucleotide encoding the signal peptide is nucleotides 1 to 63 of SEQ ID NO: 5. In another aspect, the polynucleotide encoding the signal peptide is nucleotides 1 to 60 of SEQ ID NO: 7. In another aspect, the polynucleotide encoding the signal peptide is nucleotides 1 to 57 of SEQ ID NO: 9.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide, which has at least 95% sequence identity to the sequence of amino acids 20 to 334 of SEQ ID NO: 2; or is a fragment of SEQ ID NO: 2, wherein the polypeptide has xylanase activity.

2. The polypeptide of claim 1, having at least 96% sequence identity to the sequence of amino acids 20 to 334 of SEQ ID NO: 2.

3. The polypeptide of claim 1, having at least 97% sequence identity to the sequence of amino acids 20 to 334 of SEQ ID NO: 2.

4. The polypeptide of claim 1, having at least 98% sequence identity to the sequence of amino acids 20 to 334 of SEQ ID NO: 2.

5. The polypeptide of claim 1, having at least 99% sequence identity to the sequence of amino acids 20 to 334 of SEQ ID NO: 2.

6. The polypeptide of claim 1, which is encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii).

7. The polypeptide of claim 1, which is a variant of the mature polypeptide of SEQ ID NO: 2, comprising a substitution, deletion, and/or insertion at one or more positions.

8. The polypeptide of claim 1, which comprises the sequence of amino acids 20 to 334 of SEQ ID NO: 2.

9. The polypeptide of claim 1, which is a fragment of SEQ ID NO: 2.

10. A composition comprising the polypeptide of claim 1 and one or more enzymes selected from the group consisting of a cellulase, a hemicellulase, a GH61 polypeptide, an expansin, an esterase, a laccase, a ligninolytic enzyme, a pectinase, a peroxidase, a protease, and a swollenin.

11. A process for degrading a cellulosic material, comprising: treating the cellulosic material with a polypeptide of claim 1, an endoglucanase, a cellobiohydrolase, a beta-glucosidase, and a GH61 polypeptide.

12. A process for producing a fermentation product, comprising:
  (a) saccharifying a cellulosic material with a polypeptide of claim 1, an endoglucanase, a cellobiohydrolase, a beta-glucosidase, and a GH61 polypeptide; and
  (b) fermenting the saccharified cellulosic material with one or more fermenting microorganisms to produce the fermentation product.

13. The process of claim 12, further comprising recovering the fermentation product.

14. A process for degrading a cellulosic material, comprising: treating the cellulosic material with a polypeptide of claim 3, an endoglucanase, a cellobiohydrolase, a beta-glucosidase, and a GH61 polypeptide.

15. A process for producing a fermentation product, comprising:
  (a) saccharifying a cellulosic material with a polypeptide of claim 3, an endoglucanase, a cellobiohydrolase, a beta-glucosidase, and a GH61 polypeptide; and
  (b) fermenting the saccharified cellulosic material with one or more fermenting microorganisms to produce the fermentation product.

16. The process of claim 15, further comprising recovering the fermentation product.

17. A process for degrading a cellulosic material, comprising: treating the cellulosic material with a polypeptide of claim 5, an endoglucanase, a cellobiohydrolase, a beta-glucosidase, and a GH61 polypeptide.

18. A process for producing a fermentation product, comprising:
  (a) saccharifying a cellulosic material with a polypeptide of claim 5, an endoglucanase, a cellobiohydrolase, a beta-glucosidase, and a GH61 polypeptide; and
  (b) fermenting the saccharified cellulosic material with one or more fermenting microorganisms to produce the fermentation product.

19. The process of claim 18, further comprising recovering the fermentation product.

* * * * *